(12) United States Patent
Heise et al.

(10) Patent No.: US 11,013,415 B2
(45) Date of Patent: May 25, 2021

(54) HYDRAULIC BED SENSOR AND SYSTEM FOR NON-INVASIVE MONITORING OF PHYSIOLOGICAL DATA

(75) Inventors: David Heise, Jefferson City, MO (US); Licet Rosales, Columbia, MO (US); Marjorie Skubic, Columbia, MO (US)

(73) Assignee: The Curators of the University of Missouri, Columbia, MO (US)

( * ) Notice: Subject to any disclaimer, the term of this patent is extended or adjusted under 35 U.S.C. 154(b) by 886 days.

(21) Appl. No.: 13/600,539

(22) Filed: Aug. 31, 2012

(65) Prior Publication Data

US 2013/0197375 A1    Aug. 1, 2013

Related U.S. Application Data

(60) Provisional application No. 61/575,931, filed on Aug. 31, 2011.

(51) Int. Cl.
| | | |
|---|---|---|
| *A61B 5/02* | (2006.01) | |
| *A61B 5/0205* | (2006.01) | |
| *A61B 5/024* | (2006.01) | |
| *A61B 5/00* | (2006.01) | |
| *A61B 5/08* | (2006.01) | |

(Continued)

(52) U.S. Cl.
CPC .......... *A61B 5/0205* (2013.01); *A61B 5/024* (2013.01); *A61B 5/0816* (2013.01); *A61B 5/1102* (2013.01); *A61B 5/113* (2013.01); *A61B 5/6892* (2013.01); *A61B 5/72* (2013.01); *A61B 2562/0247* (2013.01)

(58) Field of Classification Search
CPC .. A61B 2562/0247; A61B 5/72; A61B 5/1102
USPC .................................................. 600/509, 513
See application file for complete search history.

(56) References Cited

U.S. PATENT DOCUMENTS

| | | |
|---|---|---|
| 4,320,766 A | 3/1982 | Alihanka et al. |
| 5,097,841 A | 3/1992 | Moriuchi et al. |

(Continued)

FOREIGN PATENT DOCUMENTS

| | | |
|---|---|---|
| CN | 2394612 | 8/2000 |
| CN | 2477135 | 2/2002 |

(Continued)

OTHER PUBLICATIONS

Shin et al, Automatic Ballistocardiogram (BCG) Beat Detection Using a Template Matching Approach, 2008, 30th Annual International IEEE EMBS Conference, 1144-1146.*

(Continued)

*Primary Examiner* — Christian Jang
(74) *Attorney, Agent, or Firm* — Thompson Coburn LLP

(57) ABSTRACT

Disclosed herein is a new and improved non-invasive bed sensing system for detecting and monitoring physiological movements such as heartbeat and respiration. The system may employ a hydraulic fluid to transduce the physiological pressures to an integrated pressure sensor and a new and improved signal processing method to identify individual cardiac pulses from the electronic signals generated by the hydraulic transducer. The system provides increased sensitivity capable of capturing quantitative pulse and respiration rates with subtle changes, ability to distinguish between instances of low pulse rate and shallow breathing, and improved comfort over existing systems.

42 Claims, 25 Drawing Sheets

(51) Int. Cl.
*A61B 5/11* (2006.01)
*A61B 5/113* (2006.01)

(56) References Cited

U.S. PATENT DOCUMENTS

| | | | |
|---|---|---|---|
| 5,844,488 A | 12/1998 | Musick | |
| 2001/0020395 A1 | 9/2001 | Hubbard | |
| 2005/0124864 A1* | 6/2005 | Mack | A61B 5/024 600/300 |
| 2005/0190062 A1 | 9/2005 | Sullivan et al. | |
| 2006/0042409 A1 | 3/2006 | Nemoto | |
| 2006/0152378 A1 | 7/2006 | Lokhorst et al. | |
| 2007/0118054 A1* | 5/2007 | Pinhas | A61B 5/1104 600/587 |
| 2007/0262247 A1 | 11/2007 | Becerra et al. | |
| 2007/0268480 A1 | 11/2007 | Kaye | |
| 2008/0077020 A1 | 3/2008 | Young et al. | |
| 2008/0169931 A1 | 7/2008 | Gentry et al. | |
| 2009/0141124 A1* | 6/2009 | Liu | A61B 5/01 348/65 |
| 2009/0178199 A1 | 7/2009 | Brauers et al. | |
| 2009/0243833 A1 | 10/2009 | Huang et al. | |
| 2010/0163315 A1 | 7/2010 | York et al. | |
| 2010/0171622 A1 | 7/2010 | Brauers et al. | |
| 2010/0256512 A1 | 10/2010 | Sullivan | |
| 2010/0302043 A1 | 12/2010 | Skubic et al. | |
| 2011/0054330 A1 | 3/2011 | Pfeiffer et al. | |
| 2011/0087113 A1 | 4/2011 | Mack et al. | |
| 2011/0306844 A1* | 12/2011 | Young | A61B 5/0816 600/300 |
| 2011/0308015 A1 | 12/2011 | Newham | |
| 2012/0053423 A1 | 3/2012 | Kenalty et al. | |
| 2012/0123279 A1* | 5/2012 | Brueser | A61B 5/1102 600/481 |

FOREIGN PATENT DOCUMENTS

| | | |
|---|---|---|
| CN | 101499106 | 8/2009 |
| CN | 101953740 | 1/2011 |
| CN | 202101963 | 1/2012 |
| DE | 10305289 | 8/2004 |
| DE | 102008011142 | 8/2009 |
| DE | 102008058781 A1 | 6/2010 |
| FR | 2865032 | 7/2005 |
| GB | 2445760 | 7/2008 |
| HR | P20041063 | 6/2007 |
| JP | 2006-288932 | 10/2006 |
| NL | 8701288 | 1/1989 |
| WO | 2008048078 | 4/2008 |
| WO | 2013033524 | 3/2013 |

OTHER PUBLICATIONS

ProHeMon, Proactive Health Monitoring: Final report of the research project in the Academy of Finland Proactive computing research program, 2006, Tampere University of Technology, Institute of Signal Processing and Tampere University Hospital, Department of Clinical Physiology, Web, Retrieved from: http://www.cs.tut.fi/~varri/prohemon/profina4.pdf.*

Heise et al., "Refinement and Evaluation of a Hydraulic Bed Sensor", 2009 Annual International Conference of the IEEE Engineering in Medicine and Biology Society, Aug. 30, 2011, pp. 4356-4360, vol. 2011.

Extended European Search Report for EP Application 12828026.0 dated Apr. 17, 2015.

Mack et al., "Development and Preliminary Validation of Heart Rate and Breathing Rate Detection Using a Passive, Ballistocardiography-Based Sleep Monitoring System", IEEE Transactions on Information Technology in Biomedicine, Jan. 2009, pp. 111-120, vol. 13, No. 1.

Wang et al., "Development of a PVDF Piezopolymer Sensor for Unconstrained In-Sleep Cardiorespiratory Monitoring", Journal of Intelligent Material Systems and Structures, Mar. 2003, pp. 185-190, vol. 14.

Watanabe et al., "Noninvasive Measurement of Heartbeat, Respiration, Snoring and Body Movements of a Subject in Bed via a Pneumatic Method", IEEE Transactions on Biomedical Engineering, Dec. 2005, pp. 2100-2107, vol. 52, No. 12.

Zhu et al., "Real-Time Monitoring of Respiration Rhythm and Pulse Rate During Sleep", IEEE Transactions on Biomedical Engineering, Dec. 2006, pp. 2553-2563, vol. 53, No. 12.

Heise, et al., "Monitoring Pulse and Respiration with a Non-Invasive Hydraulic Bed Sensor", 32nd Annual International of the IEEE EMBS, Aug. 31-Sep. 4, 2010, pp. 2119-2123, Buenos Aires, Argentina Conference.

International Search Report and Written Opinion for corresponding PCT/US2012/053325 dated Nov. 16, 2012.

Rosales et al., "Exploring Passive Heartbeat Detection Using a Hydraulic Bed Sensor System", A Thesis presented to the Faculty of the Graduate School University of Missouri-Columbia, Dec. 2011, pp. 1-172, Columbia, Missouri, USA.

Rosales et al., "Heartbeat Detection from a Hydraulic Bed Sensor Using a Clustering Approach", 34th Annual Int'l Conf. of the IEEE EMBS, San Diego, CA Aug. 28-Sep. 1, 2012, pp. 2383-2387.

* cited by examiner

Results of Evaluation Trial Processing the Signal with Varying Algorithm Parameters

| | A | B | C | D | E | F | G | H | I | J | K | L |
|---|---|---|---|---|---|---|---|---|---|---|---|---|
| | ws=150 | | | ws=250 | | | ws=400 | | | ws=600 | | |
| | f=1 Hz | f=1.5 Hz | f=2 Hz | f=1 Hz | f=1.5 Hz | f=2 Hz | f=1 Hz | f=1.5 Hz | f=2 Hz | f=1 Hz | f=1.5 Hz | f=2 Hz |
| Subject #1 | | | | | | | | | | | | |
| <2 | 16.67 | 69.05 | 59.52 | 16.67 | 69.05 | 73.81 | 16.67 | 57.14 | 69.05 | 16.67 | 33.33 | 57.14 |
| =2 | 0.00 | 11.90 | 23.81 | 0.00 | 11.90 | 19.05 | 0.00 | 14.29 | 23.81 | 0.00 | 14.29 | 21.43 |
| >2 | 83.33 | 19.05 | 16.67 | 83.33 | 19.05 | 7.14 | 83.33 | 28.57 | 7.14 | 83.33 | 52.38 | 21.43 |
| Subject #2 | | | | | | | | | | | | |
| <2 | 17.50 | 90.00 | 40.00 | 17.50 | 87.50 | 40.00 | 17.50 | 62.50 | 60.00 | 17.50 | 57.50 | 57.50 |
| =2 | 5.00 | 2.50 | 15.00 | 5.00 | 2.50 | 17.50 | 2.50 | 27.50 | 17.50 | 2.50 | 12.50 | 15.00 |
| >2 | 77.50 | 7.50 | 45.00 | 77.50 | 10.00 | 42.50 | 80.00 | 10.00 | 22.50 | 80.00 | 30.00 | 27.50 |
| Subject #3 | | | | | | | | | | | | |
| <2 | 24.39 | 70.73 | 26.83 | 24.39 | 75.61 | 39.02 | 21.95 | 65.85 | 53.66 | 17.07 | 48.78 | 43.90 |
| =2 | 9.76 | 21.95 | 12.20 | 4.88 | 7.32 | 9.76 | 2.44 | 21.95 | 14.63 | 2.44 | 21.95 | 29.27 |
| >2 | 65.85 | 7.32 | 60.98 | 70.73 | 17.07 | 51.22 | 75.61 | 12.20 | 31.71 | 80.49 | 29.27 | 26.83 |
| Subject #4 | | | | | | | | | | | | |
| <2 | 25.64 | 92.31 | 89.74 | 25.64 | 87.18 | 92.31 | 25.64 | 79.49 | 79.49 | 25.64 | 41.03 | 74.36 |
| =2 | 0.00 | 2.56 | 5.13 | 0.00 | 5.13 | 2.56 | 0.00 | 12.82 | 15.38 | 0.00 | 25.64 | 15.38 |
| >2 | 74.36 | 5.13 | 5.13 | 74.36 | 7.69 | 5.13 | 74.36 | 7.69 | 5.13 | 74.36 | 33.33 | 10.26 |
| Subject #5 | | | | | | | | | | | | |
| <2 | 40.00 | 87.50 | 52.50 | 40.00 | 82.50 | 52.50 | 32.50 | 82.50 | 62.50 | 25.00 | 57.50 | 47.50 |
| =2 | 15.00 | 10.00 | 7.50 | 10.00 | 17.50 | 15.00 | 12.50 | 10.00 | 10.00 | 5.00 | 15.00 | 17.50 |
| >2 | 45.00 | 2.50 | 40.00 | 50.00 | 0.00 | 32.50 | 55.00 | 7.50 | 27.50 | 70.00 | 27.50 | 35.00 |

Figure 21

Heartbeat Detection Confusion Matrices

| Subject | Actual class | T1 | | T2 | | | T3 | | | | | | T4 | | | | | |
|---|---|---|---|---|---|---|---|---|---|---|---|---|---|---|---|---|---|---|
| | | B1 | | B2 | | B3 | | B1 | | B2 | | B3 | | B1 | | B2 | | B3 | |
| | | HB | NHB | HB | NHB | HB | NHB | HB | NHB | HB | NHB | HB | NHB | HB | NHB | HB | NHB | HB | NHB |
| 1 | HB | 120 | 0 | 120 | 0 | 81 | 1 | 120 | 0 | 119 | 0 | 81 | 1 | 120 | 0 | 120 | 0 | 79 | 2 |
| | NHB | 10 | 332 | 11 | 330 | 25 | 218 | 1 | 340 | 0 | 334 | 0 | 226 | 2 | 380 | 0 | 356 | 1 | 238 |
| | CC(%) | 97.8 | | 97.6 | | 92.0 | | 99.8 | | 100.0 | | 99.7 | | 99.6 | | 100.0 | | 99.1 | |
| 2 | HB | | | | | | | 147 | 6 | 182 | 3 | 123 | 3 | | | | | | |
| | NHB | | | | | | | 4 | 538 | 6 | 626 | 3 | 472 | | | | | | |
| | CC(%) | | | | | | | 98.6 | | 98.9 | | 97.9 | | | | | | | |
| 3 | HB | | | | | | | 110 | 0 | 110 | 0 | 90 | 0 | 110 | 0 | 111 | 3 | 88 | 3 |
| | NHB | | | | | | | 54 | 443 | 91 | 428 | 74 | 324 | 0 | 494 | 3 | 496 | 1 | 435 |
| | CC(%) | | | | | | | 91.0 | | 85.5 | | 84.8 | | 100.0 | | 99.5 | | 99.4 | |
| 4 | HB | | | | | | | | | | | | | 51 | 57 | 85 | 24 | 64 | 28 |
| | NHB | | | | | | | | | | | | | 11 | 365 | 111 | 245 | 6 | 314 |
| | CC(%) | | | | | | | | | | | | | 86.0 | | 71.0 | | 92.2 | |

Predicted class

Figure 27

HYDRAULIC BED SENSOR AND SYSTEM FOR NON-INVASIVE MONITORING OF PHYSIOLOGICAL DATA

CROSS-REFERENCE AND PRIORITY CLAIM TO RELATED PATENT APPLICATION

This patent application claims priority to U.S. patent application Ser. No. 61/575,931, filed Aug. 31, 2011, entitled "Hydraulic Bed Sensor", the entire disclosure of which is incorporated herein by reference.

GRANT STATEMENT

This invention was made with Government support under Grant No. IIS-0428420 and Grant No. CNS-0931607 from the National Science Foundation (NSF). The Government has certain rights in the invention.

INTRODUCTION

Ballistocardiography (BCG), which records the movements imparted to the body by the forces associated with contraction of the heart and acceleration and deceleration of blood as it is ejected and moved in large vessels, is believed to be a promising tool for non-invasive monitoring of physiological data. These mechanical motions due to cardiac and hemodynamic events can be recorded from multiple locations and with multiple types of sensors, leading to a confusing number of techniques and signals, sometimes related and sometimes not. To help alleviate such confusion, a standardized terminology has emerged to describe ballistocardiogram waves as set forth in connection with FIG. 29. As shown in FIG. 29, the ballistocardiogram waves may be separated in three major groups, the pre-systolic (frequently disregarded), the systolic and the diastolic.

For the pre-systolic group, there are:
  F wave (rarely seen)—headward wave preceding G (see FIG. 29), related to pre-systolic events not an after vibration.
  G wave (see FIG. 29)—small footward wave which at time precedes the H wave.
For the systolic group, there are:
  H wave (see FIG. 29)—headward deflection that begins close to the peak of the R wave (from the electrocardiogram), the maximum peak synchronously or near the start of ejection.
  I wave (see FIG. 29)—footward deflection that follows the H wave, occurs early in systole. The I wave can also be referred to as an ejection wave.
  J wave (see FIG. 29)—largest headward wave the immediately follows the I wave; occurs late in systole. The J wave can also be referred to as an ejection wave.
  K wave (see FIG. 29)—footward wave following the J wave; occurs before the end of systole.
For the diastolic group, there are:
  L and N waves—two smaller headward deflections which usually follow K (see FIG. 29 for L wave)
  M wave (see FIG. 29)—footward deflection between L and N. Furthermore, it should be understood that smaller subsequent waves may be visible, and these are typically named in sequence.

Non-invasive monitoring of physiological data of a subject, especially an in-bed patient or an elderly person, plays an important role in supporting the continuous efforts of in-home care. Particularly, long-term monitoring of the elderly via sensing technologies is emerging as a strategy for detecting early signs of illness and functional decline. It is anticipated that such an approach may provide opportunities for appropriate interventions that will contribute to maintaining health, quality-of-life, and independence.

In comparing sensor data changes to health changes, the bed sensor has proven to be a useful component of the sensor network. However, the inventors believe that room for improvement exists with such technologies with respect to their sensitivities in detecting physiological data and providing comfort to users.

In an effort to address such needs, the inventors disclose a health monitoring system, the system comprising: (1) a hydraulic sensor for positioning with respect to a living being to non-invasively sense a signal, the signal comprising a heartbeat component indicative of a heartbeat pattern for the living being and a respiratory component indicative of a respiratory pattern for the living being, and (2) a processor for receiving the sensor signal, the processor configured to analyze data representative of the sensor signal to generate extracted heartbeat data. The inventors further disclose a method comprising: (1) hydraulically transducing physiological movement of a living being to sense a signal, the signal comprising a heartbeat component indicative of a heartbeat pattern for the living being and a respiratory component indicative of a respiratory pattern for the living being, and (2) processing, by a processor, the sensed signal, the processing including the processor extracting heartbeat data from data representative of the sensor signal. With such a system and method, the processor can employ various techniques to extract the heartbeat data; for example windowed peak-to-peak deviation (WPPD) analysis and clustering analysis.

The inventors further disclose a health monitoring system, the system comprising: (1) a hydraulic sensor for positioning with respect to a living being to non-invasively sense a signal, the signal comprising a heartbeat component indicative of a heartbeat pattern for the living being and a respiratory component indicative of a respiratory pattern for the living being, and (2) a processor for receiving the sensor signal, the processor configured to (i) process the sensor signal to generate heartbeat data and respiratory data for the living being, and (ii) store the generated heartbeat and respiratory data in a database for subsequent analysis.

In accordance with yet another exemplary aspect, the inventors disclose an apparatus comprising a processor for receiving a sensor signal, the signal comprising a heartbeat component indicative of a heartbeat pattern for a living being and a respiratory component indicative of a respiratory pattern for the living being, the processor configured to apply a windowed peak-to-peak deviation (WPPD) analysis to data representative of the sensor signal to generate extracted heartbeat data.

In accordance with still another exemplary aspect, the inventors disclose an apparatus comprising a processor for receiving a sensor signal, the signal comprising a heartbeat component indicative of a heartbeat pattern for a living being and a respiratory component indicative of a respiratory pattern for the living being, the processor configured to apply a clustering analysis to data representative of the sensor signal to generate extracted heartbeat data.

Furthermore, the inventors disclose a computer program product comprising a plurality of computer-executable instructions resident on a non-transitory computer-readable storage medium for execution to process data representative of a sensor signal, the signal comprising a heartbeat component indicative of a heartbeat pattern for a living being and a respiratory component indicative of a respiratory pattern for the living being, the instructions configured to analyze the data representative of the sensor signal to generate extracted heartbeat data.

Further still, the inventors disclose a sensor comprising: (1) a hydraulic transducer for positioning with respect to a living being to non-invasively sense a signal, the signal comprising a heartbeat component indicative of a heartbeat pattern for the living being and a respiratory component indicative of a respiratory pattern for the living being, and (2) a pressure sensor, wherein the hydraulic transducer is configured to apply fluid pressure to the pressure sensor in response to the heartbeat and respiratory patterns of the living being.

These and other features and advantages of the invention will be in part apparent and in part pointed out in the following description and referenced figures.

BRIEF DESCRIPTION OF DRAWINGS

FIG. 21 shows a table of results for various WPPD algorithm parameters.

FIG. 27 shows a results table for heartbeat detection confusion matrices using the k-means clustering algorithm.

DETAILED DESCRIPTION

The invention provides a new and improved non-invasive bed sensing system to detect and monitor small scale physiological movements, such as breathing and heartbeat. Exemplary embodiments disclosed herein employ a hydraulic fluid to transduce the physiological pressures to an integrated pressure sensor. Signal processing techniques can employ techniques such as windowed peak-to-peak deviation (WPPD) and/or clustering to identify physiological data such as windowed instantaneous heart rates, individual cardiac pulses, respiration, restlessness, or other parameters from the electronic signals generated by the hydraulic transducer. These electronic signals will contain a cardiac component (attributable to the subject's heartbeat), a respiratory component (attributable to the subject's breathing motions), and a noise component (attributable to sources other than heartbeats and breathing). The signal processing techniques can be configured to extract the relevant cardiac information from the sensor signal as well as the relevant respiratory information from the sensor signal in order to gauge physiological data such as one or more of a heart rate, respiratory rate, and restlessness.

Figure 1:
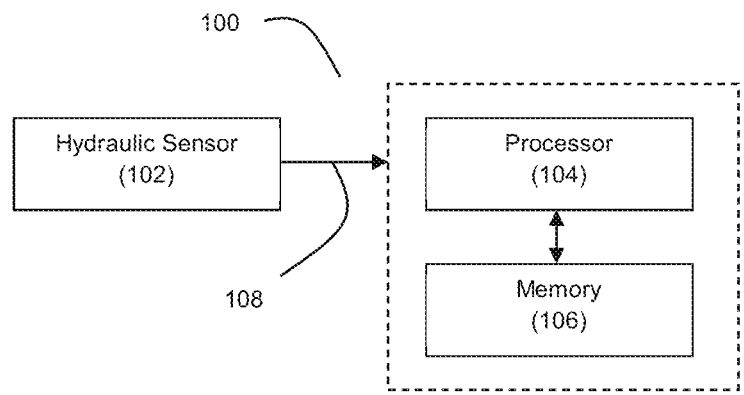
FIG. 1 shows an exemplary system employing a hydraulic sensor to sense physiological movement of a living being.

FIG. 1 illustrates an exemplary sensing system 100 in accordance with an embodiment of the invention. The system 100 comprises a hydraulic sensor 102 in communication with a processor 104 and memory 106. The hydraulic sensor 102 senses small-scale physiological movements of a person and provides a sensor signal 108 to the processor 104 and memory 106. The hydraulic sensor 102, processor 104, and memory 106 cooperate together to generate data that measures a person's physiological patterns over time. For example, the hydraulic sensor 102, processor 104, and memory 106 cooperate together to generate data that measures a person's respiratory rate. As another example, the hydraulic sensor 102, processor 104, and memory 106 cooperate together to generate data that measures a person's heartbeat rate. As another example, the hydraulic sensor 102, processor 104, and memory 106 cooperate together to generate data that measures a person's restlessness. Furthermore, it should also be understood that the hydraulic sensor 102, processor 104, and memory 106 cooperate together to generate data that measures any combination of the foregoing.

Figure 2A:
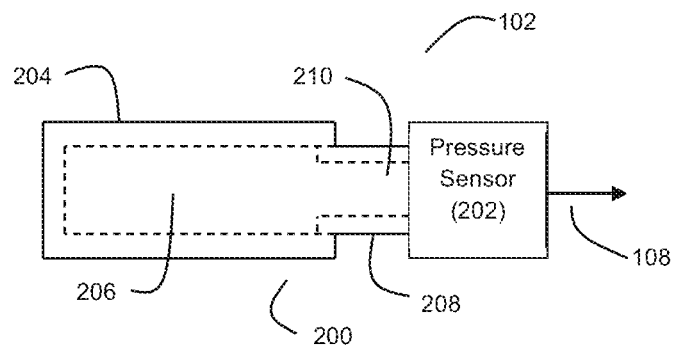
FIGS. 2(a) and (b) show an exemplary embodiment for a hydraulic sensor.

FIG. 2(a) depicts an exemplary embodiment for the hydraulic sensor 102. The hydraulic sensor 102 may comprise a hydraulic transducer 200 in communication with a pressure sensor 202.

The hydraulic transducer 200 may comprise a deformable vessel 204 having a cavity 206 filled with a fluid such as water. One end portion of the vessel can be closed or sealed while another end portion can be open to permit the passage of the fluid. A connector 208 can be used to provide a connection between the vessel 204 and the pressure sensor 202. Thus, as a person's movement impacts that hydraulic transducer, fluid will flow within the cavity 206 and through the channel 210 of the connector 208 to apply fluid pressure to the pressure sensor 202. However, it should be understood that the pressure sensor 202 could also be directly connected to the open end portion of the vessel 204.

In response to the applied fluid pressure, the pressure sensor thus generates the sensor signal 108 that is representative of the movement that impacted the hydraulic transducer 200. As explained below, the sensor signal 108 will comprise a respiratory or breathing component, a heart rate or cardiac component, and a noise component. Pressure sensor 202 may take the form of any suitable pressure sensor featuring a usable range (such as 0 to 10 kPa) sufficient to handle the range of pressures transmitted from the weight of the body (plus mattress, cushion, or other intermediary element between the person and the sensor 102) through the hydraulic transducer 200 while remaining sensitive enough to detect low-amplitude variations (such as heartbeat). The pressure sensor 202 may also feature on-chip calibration and compensation, and be configured to generate an output signal between 0 to 5 volts, suitable for sampling as described below. For example, a small integrated silicon pressure sensor such as the Freescale MPX5010GS or MPX5010GP pressure sensor available from Freescale Semiconductor Inc. of Austin, Tex. could be used. The sensor signal 108 can be communicated from the pressure sensor 202 to the processor 204 via any suitable medium, such as a wired connection between the two.

Figure 2B:
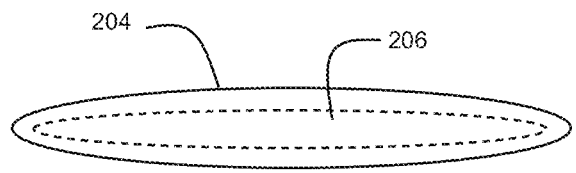

As shown in FIG. 2(b) for an exemplary embodiment, the deformable vessel 204 for the hydraulic transducer 200 may exhibit a flat profile. With such a design, the hydraulic sensor 102 is expected to provide greater comfort to a person during use. For example, when placed under a mattress, pillow or cushion, the hydraulic sensor 102 would thereby provide less deformation of the mattress, pillow or cushion to help make the hydraulic sensor less perceptible, or even virtually imperceptible, to a person.

The hydraulic transducer may also include one or more valves configured to permit fluid to be added to/removed from and/or permit air to bleed from the vessel. Further still, for an exemplary embodiment, it is desired that the hydraulic sensor 102 be configured to watertight.

The inventors have constructed various prototypes for the hydraulic transducer 200 using commonly-available materials. With an exemplary first prototype, a three-inch wide (7.6 cm) discharge hose was used as the deformable vessel 204. Such a hose maintains a very flat profile even when containing fluid. A hose length of approximately 1.3 meters was used to stretch across the width of a standard twin mattress, which was used in one aspect of the testing. PVC endcaps were fitted to the discharge hose with hose clamps, and the endcaps were drilled to accept brass fittings. The sealed end portion was fitted a port with a valve, to allow addition/removal of water and air. The open end portion was fitted a brass nipple, to which a length of 0.170" (4.3 mm, inside diameter) vinyl tubing was attached to serve as connector 208. Approximately 1.5 meters of this small diameter tubing connected the body of the transducer 200 to a Freescale MPX5010GS pressure sensor 202. After construction, water was added to the hydraulic transducer 200, and air was bled from the cavity 206. With a second prototype, PVC cement was used to seal one end of the discharge hose completely, with the other open end being sealed except for a short length (6 cm) of small (2.8 mm inside diameter) vinyl tubing to provide a port connection for attachment to the pressure sensor 202. With a third exemplary prototype, the length and volume for the fluid in the vessel were approximately 22 inches and 14 ounces respectively.

Figure 3:
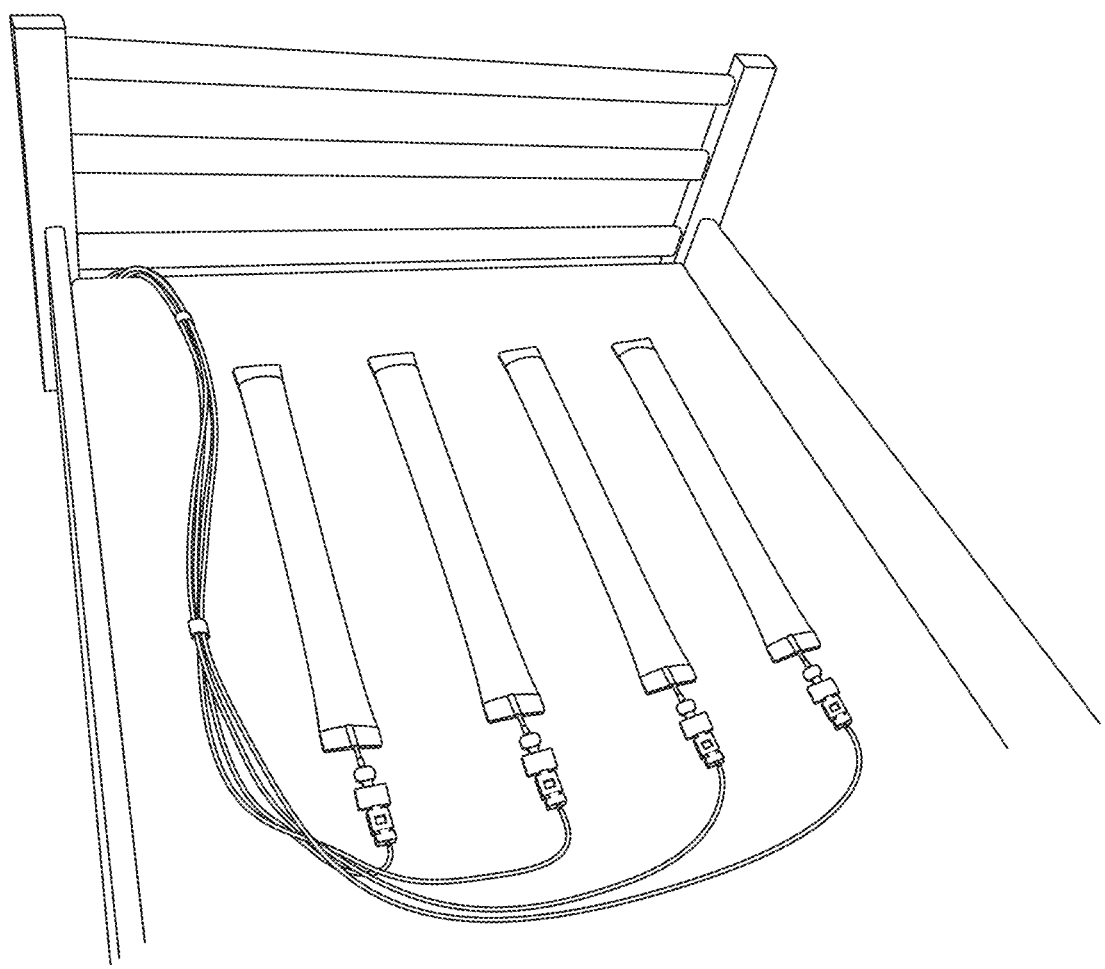
FIG. 3 shows an exemplary positioning of an exemplary hydraulic sensor with respect to a bed.
Figure 4:
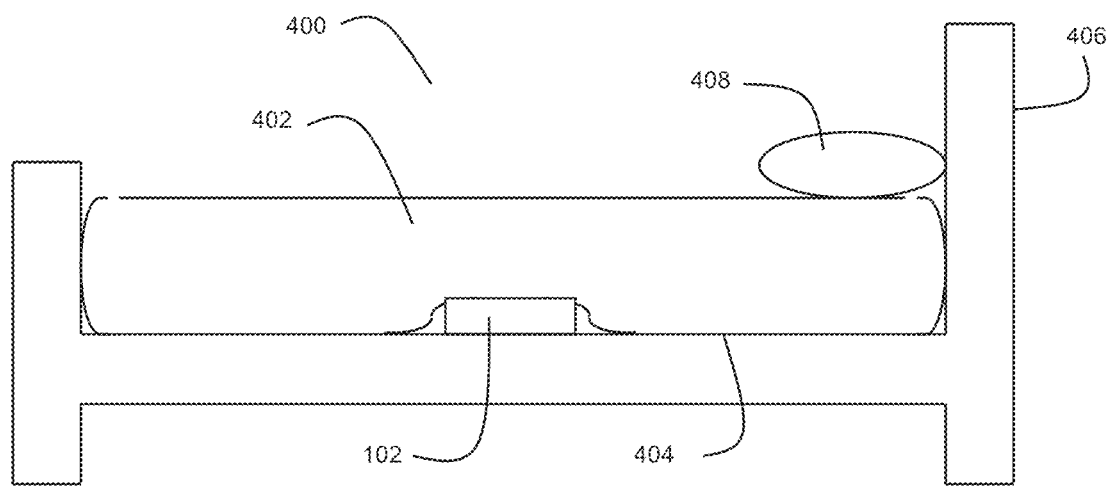
FIG. 4 shows another exemplary positioning of the hydraulic sensor with respect to a bed.

Furthermore, the hydraulic sensor may comprise a plurality of the hydraulic transducers 200/pressure sensors 202. As an example, FIG. 3 is a picture showing an exemplary arrangement where 4 of the hydraulic transducers 200/pressure sensors 202 are deployed, although other arrangements could be employed (see Rosales, L., "Exploring Passive Heartbeat Detection Using a Hydraulic Bed System", Master's Thesis, University of Missouri-Columbia, the entire disclosure of which is incorporated herein by reference). It is preferred that the hydraulic transducer 200 and pressure sensor 202 be placed under a subject's mattress, pillow, or cushion for improved comfort and easy installation. However, it should be understood that placement elsewhere in proximity to the person (for example above the mattress, pillow, or cushion) could be employed if desired. For example, as also shown in FIG. 4, the hydraulic sensor 102 can be positioned in a bedroom 400 on a top surface of the bed frame 406 in a location contacting an underside 404 of a mattress 402. The hydraulic sensor 102 could also be positioned beneath pillow 408. In an exemplary embodiment, a sensor signal 108 representative of a person's physiological state is obtained when the hydraulic sensor 102 is positioned under the mattress 402 within a close vicinity of where a subject's torso would lie (for example, within a distance of 1.5 to 4 feet from the head board of the bed). Horizontal, vertical, or other positioning of the hydraulic sensor 102 may be selected based on factors such as the type and size of the mattress, the size of the body, etc. The example of FIG. 3, shows the hydraulic transducers 200 being positioned vertically (or along the length of the bed). In a horizontal deployment, the hydraulic transducers 200 can be placed across the width of the bed. When the transducer is placed under a pillow/cushion, it may be placed across the center region of the pillow or cushion.

Experimentation by the inventors (see the above-referenced and incorporated Master's thesis "Exploring Passive Heartbeat Detection Using a Hydraulic Bed System") has indicated to the inventors that the hydraulic sensor 102 can effectively capture heartbeat data when the hydraulic sensor 102 is located between 7 inches and 25 inches from the headboard of a bed (which as noted above, corresponds approximately to the location of the torso when lying on a bed in a normal position). Furthermore, for an embodiment where the length of the hydraulic transducer 200 is approximately 22 inches, the hydraulic transducer 200, in a vertical deployment (as shown in FIG. 3), can be positioned to span from around 2 inches from the headboard to around 24 inches from the headboard. However, it should be understood that other positioning could be employed.

In a vertical deployment as shown in FIG. 3, it is believed that the heartbeat signal can be effectively captured because less of at least one of the hydraulic transducer's area will be pressed on by body parts other than the torso, such as shoulders and arms, thereby allowing at least one of the transducers to primarily capture chest movements. Additionally, the primary force being captured by the ballistocardiogram is the axial (with respect to the body) force of blood being ejected through the aorta. Since monitoring during sleep is desired, the use of multiple, vertically-deployed, hydraulic transducers 200 can be added in order to cover the width of the bed. The spacing between transducers 200 can be defined as a function of the neck-to-shoulder distance of the person being monitored such that two or more of the hydraulic transducers 200 would capture the heartbeat signals with the person lying on his/her back and at least one of the hydraulic transducers 200 would capture the heartbeat signals with the person lying on his/her left or right side. However, it should be understood that other spacing arrangements between the multiple hydraulic transducers 200 could be employed.

The processor 104 and memory 106 can take any of a number of forms. The processor 104 may comprise a hardware subsystem such as circuit board for processing the sensor signal and a microprocessor or the like for executing software to generate physiological data from the processed sensor signal. The processor and memory may also take the form of an embedded microcontroller that is configured to provide both signal processing and data analysis.

Extracting Heartbeat Information from the Sensor Signal

Various techniques may be employed to extract the heartbeat information from the sensor signal. In a first exemplary embodiment, a windowed peak-to-peak deviation (WPPD) analysis is employed. In a second exemplary embodiment, a clustering technique such as k-means clustering analysis is employed.

Figure 5:
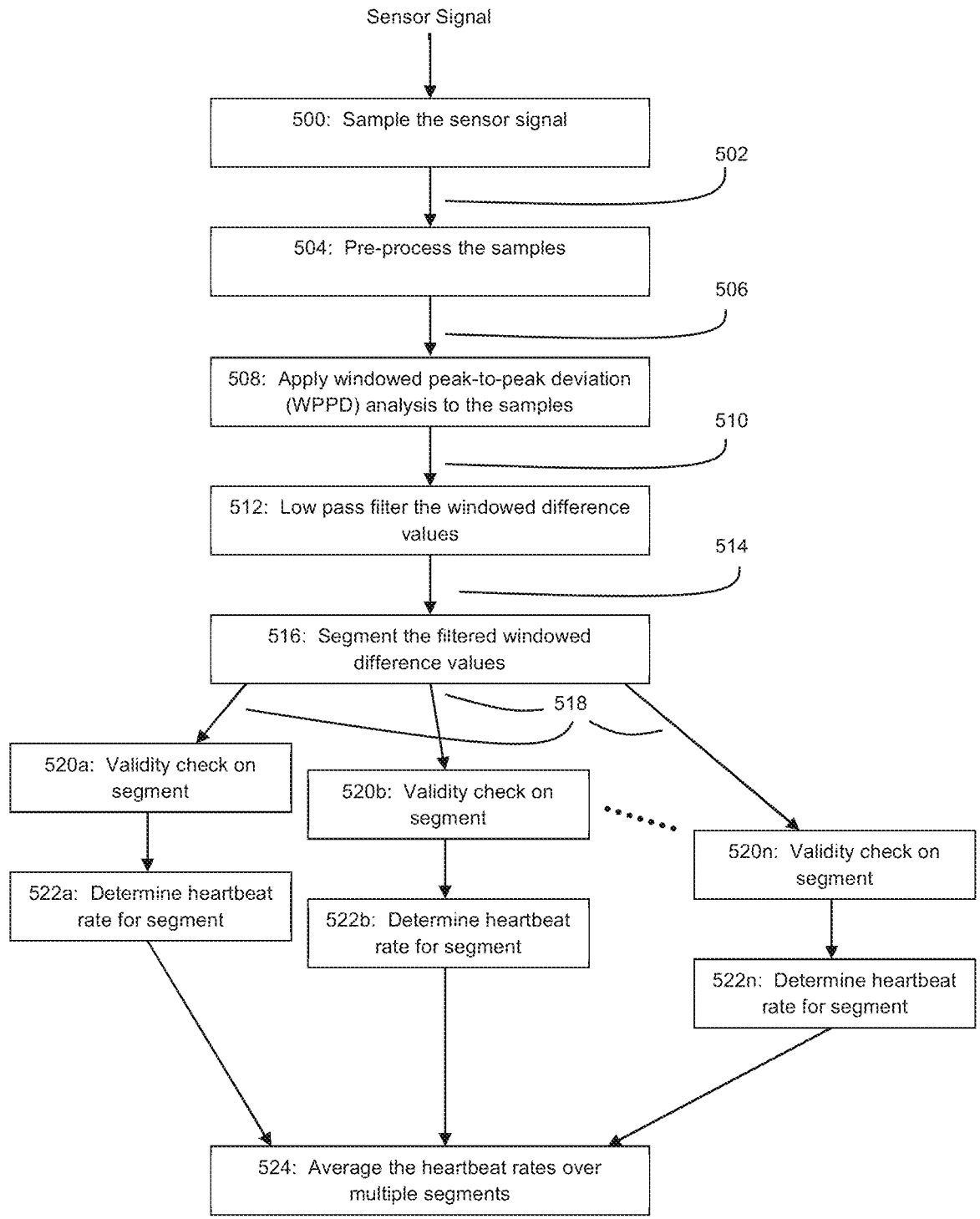
FIG. 5 shows an exemplary process flow for extracting heartbeat data from a sensor signal using a WPPD analysis.

FIG. 5 illustrates an exemplary process flow for the processor 104 and memory 106 to extract heart rate data from the sensor signal using a WPPD analysis.

At step 500, the processor samples the sensor signal 108. The exemplary sensor signal 108 may have a voltage ranging between 0 and 5 volts. This voltage signal is expected to contain a large amount of high frequency noise. To address this high frequency noise, the sensor signal is sampled to generate a plurality of digital samples that are representative of the sensor signal.

Figure 6A:
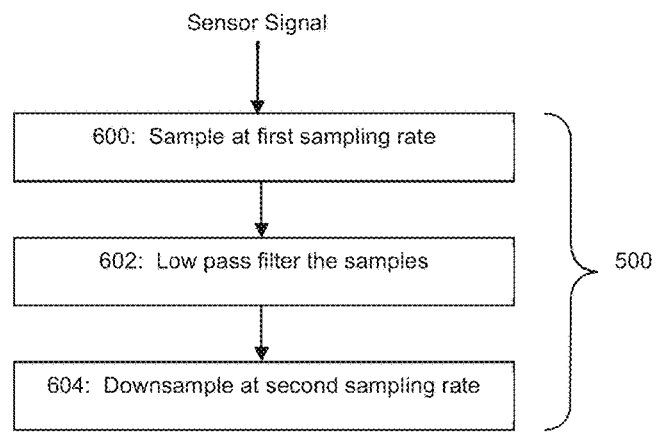
FIGS. 6(a) and (b) show exemplary techniques for sampling the sensor signal.
Figure 6B:
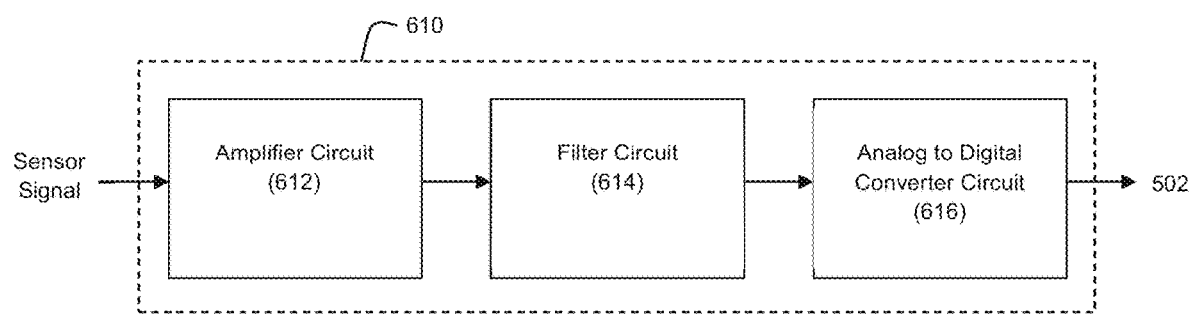
Figure 12:
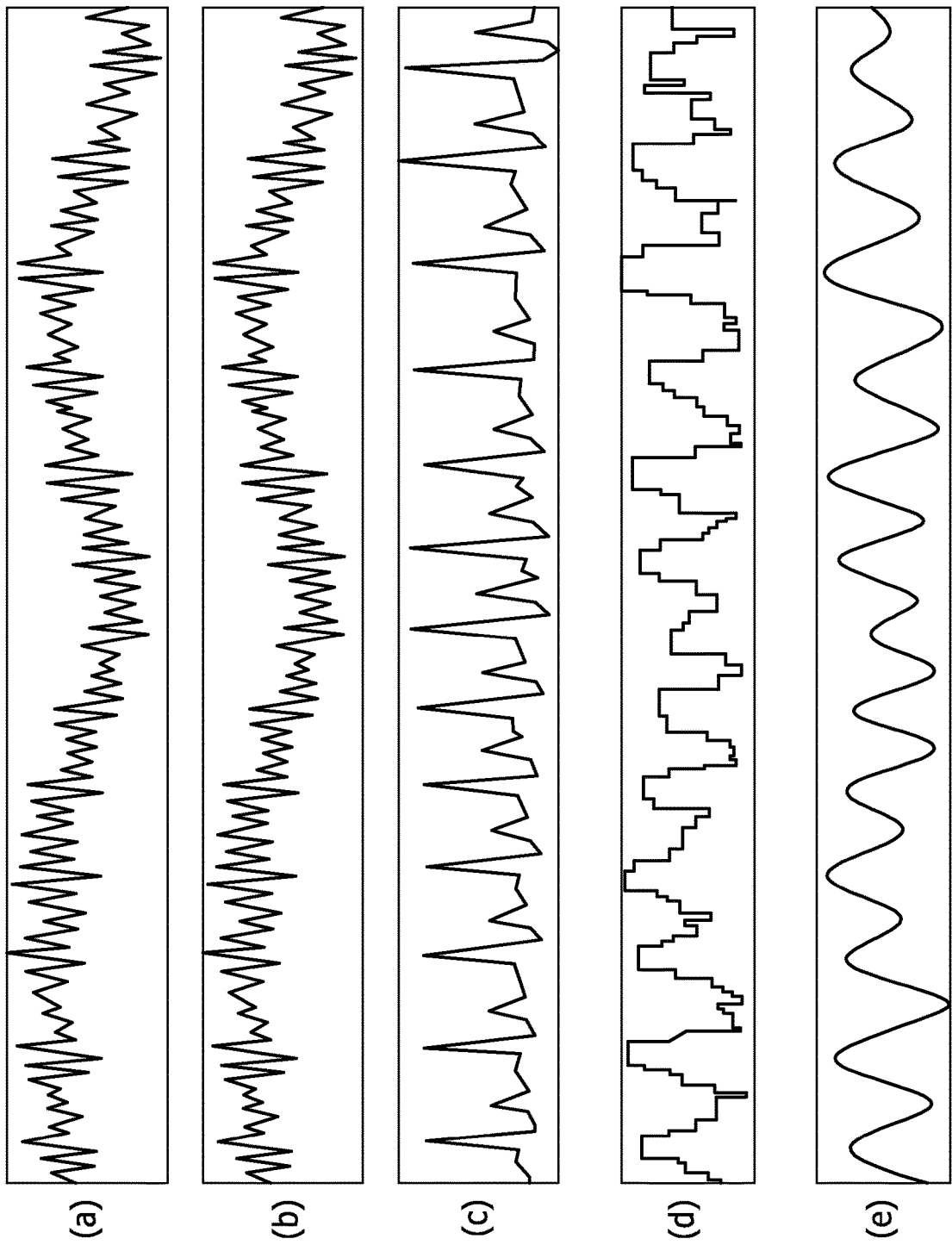
FIG. 12 shows exemplary signals at various stages of the process flow for the heartbeat extraction algorithm of FIG. 5.

FIG. 6(a) illustrates an exemplary embodiment for the sampling operation 500. In the example of FIG. 6(a), the sensor signal 108 is sampled at a first sampling rate (e.g., 10 kHz) via a 12-bit analog-to-digital converter (ADC) (step 600). Then, the samples are low pass filtered (step 602) and downsampled at a second sampling rate (step 604) to 100 Hz for further processing. FIG. 12(a) illustrates an exemplary 10 second segment of signal 502 for the output of step 500. The steps of FIG. 6(a) may be performed in software. However, it should also be understood that the sampling step 500 can be implemented in hardware as shown in FIG. 6(b). FIG. 6(b) shows an exemplary hardware circuit 610 that comprises an amplifier circuit 612, a filter circuit 614, and an ADC circuit 616. The amplifier circuit 612 can be configured to provide amplification of the sensor signal 108 by a factor of 10 using a 741 op-amp. The filter circuit 614 can be configured to provide anti-aliasing and noise reduction via an $8^{th}$-order integrated Bessel filter (e.g., a Maxim MAX7401) with a corner frequency of 38 Hz. The ADC circuit 616 can be configured to provide 12-bit ADC at a sampling rate of 100 Hz. By employing a hardware circuit such as that of FIG. 6(b), one can directly sample at 100 Hz and eliminate a need to sample at a much higher frequency and then filter and downsample in software.

The samples of signal 502 are then pre-processed at step 504. This step can optionally be performed in software executed by a processor. This pre-processing can include low pass filtering, and such low pass filtering operation can employ a cutoff frequency of around 10 Hz while maintaining 100 samples per second. FIG. 12(b) illustrates an exemplary output signal 506 from this low pass filtering operation. It should also be understood that the 20 Hz cutoff frequency for this step is exemplary only. It is believed that a range of around 5 Hz to around 20 Hz can be used as the cutoff frequency.

The filtered samples of signal 506 are then subjected to a windowed peak-to-peak deviation (WPPD) analysis at step 508. Visual observation of the low-pass filtered signal (see FIG. 12(b)) shows a clear breathing component (approximately two breaths over the 10 seconds shown), but the heartbeat is less obvious. Only after comparison to the corresponding heartbeat signal (see FIG. 12(c) which shows a heartbeat signal reference detected by a pulse sensor attached to a subject's finger used as a ground truth) can one see where heartbeats are present. These heartbeats are not easily separated in frequency, but with careful observation one can see that at each heartbeat the signal has a greater deviation from the most negative voltage to the most positive voltage within a small window, i.e., peak-to-peak. As such, the inventors believe that a WPPD analysis will greatly improve the sensitivity of the system to extract a person's heartbeat from the sensor signal 108.

Figure 7:
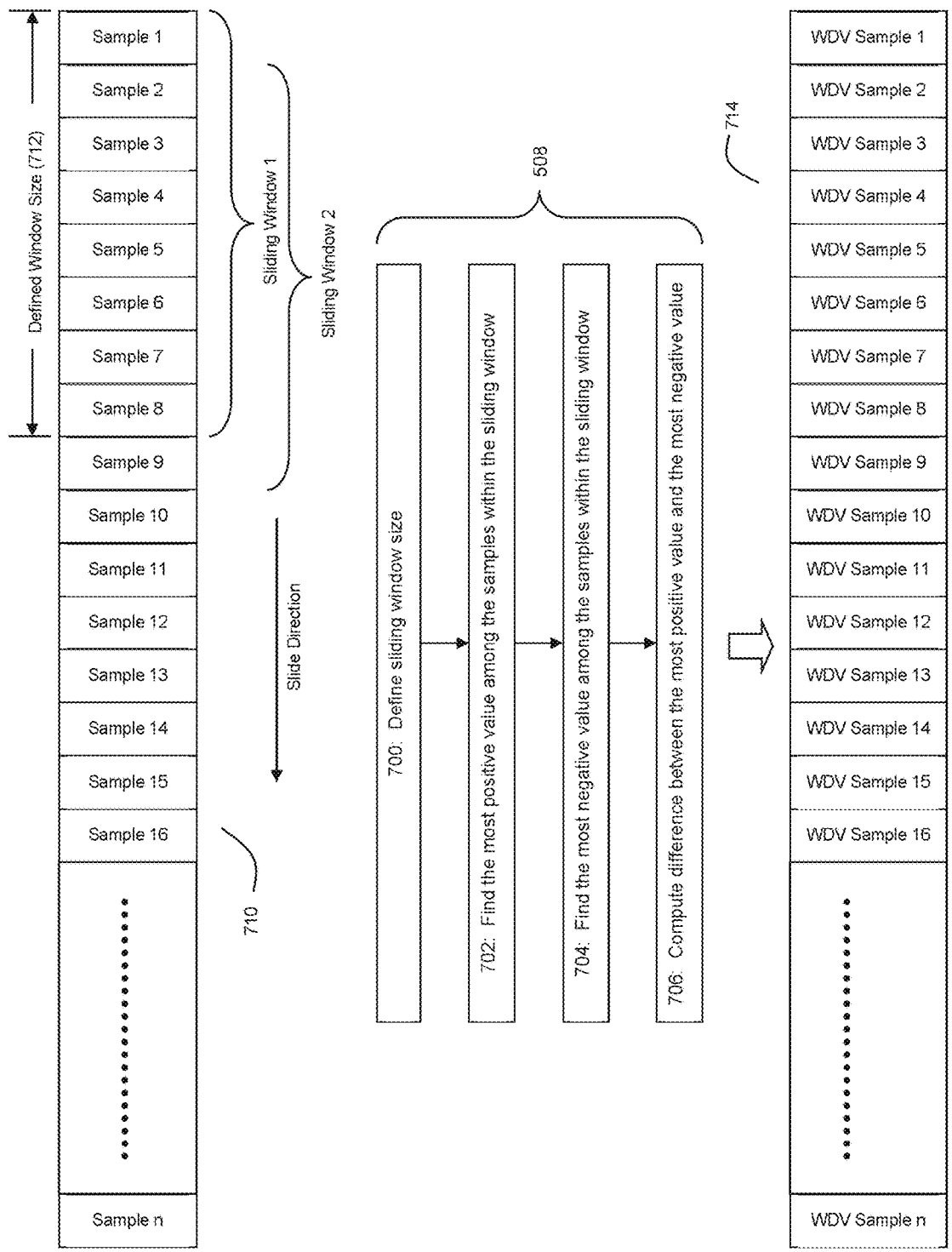
FIG. 7 shows an exemplary technique for applying the WPPD analysis.

FIG. 7 depicts an exemplary process flow for performing the WPPD analysis of step 508. As an input, the samples 710 serve as the filtered samples of signal 506. At step 700, a size for a sliding window 712 is defined. An exemplary sliding window size, ws, can be set as 25 samples. However, it should be well understood that other values can be used, particularly in instances where a high pulse rate is expected, in which case a shorter sliding window may be desirable. Furthermore, it should be understood that the value for ws could be varied on a case-by-case basis as explained below.

At step 702, the processor finds the most positive sample value among the samples in the sliding window. At step 704, the processor finds the most negative value among the samples in the sliding window. The most positive sample value can be described as the maximum value while the most negative value can be described as the minimum value. Furthermore, in embodiments where the values of the samples do not have positive and negative values (e.g., the scale for the sample values is a range of positive values), steps 702 and 704 would be configured to find the values with the largest and smallest magnitudes (again, these can be described as the maximum and minimum values). Next, at step 706, the processor computes the difference between the maximum and minimum sample values within the sliding window. This difference value can be referred to as the windowed difference value (WDV). The equation below further elaborates on the computations involved by steps 702-706:

$$WDV(t)=MAX_{i=t}^{t+ws}[signal(i)]-MIN_{i=t}^{t+ws}[signal(i)]$$

where WDV(t) represents the WDV for the samples i within sliding window t. As the sliding window slides in the direction shown in FIG. 7, the processor will continue to compute new WDV values for the subsequent windows. The output of step 706 is thus a series of WDV samples 714 as shown in FIG. 7. FIG. 12(d) shows the exemplary signal 510 (comprised of multiple WDV samples 714) that results from the operation of step 508.

As shown by FIG. 12(d), the WDV samples clearly indicate the occurrence of the heartbeats, but further filtering may be desired to reduce the effect of noise and smooth the signal. Thus, returning to FIG. 5, at step 512 the processor performs low pass filtering on the WDV samples of signal 510. This low pass filtering can employ a cutoff frequency, f, of around 4 Hz, which is expected to be sufficient for heart rates up to 240 beats per minute (bpm). FIG. 12(e) illustrates an exemplary output signal 514 from this low pass filtering operation. This signal is thus comprised of a series of filtered WDV samples (or FWDV samples). It should be understood that the value for the cutoff frequency f of step 512 can be a fixed predetermined value or it can be varied to meet the needs of a particular application (e.g., customized to a particular person) as explained below. An exemplary range of values for this cutoff frequency is around 1 Hz to around 4 Hz.

Figure 8:
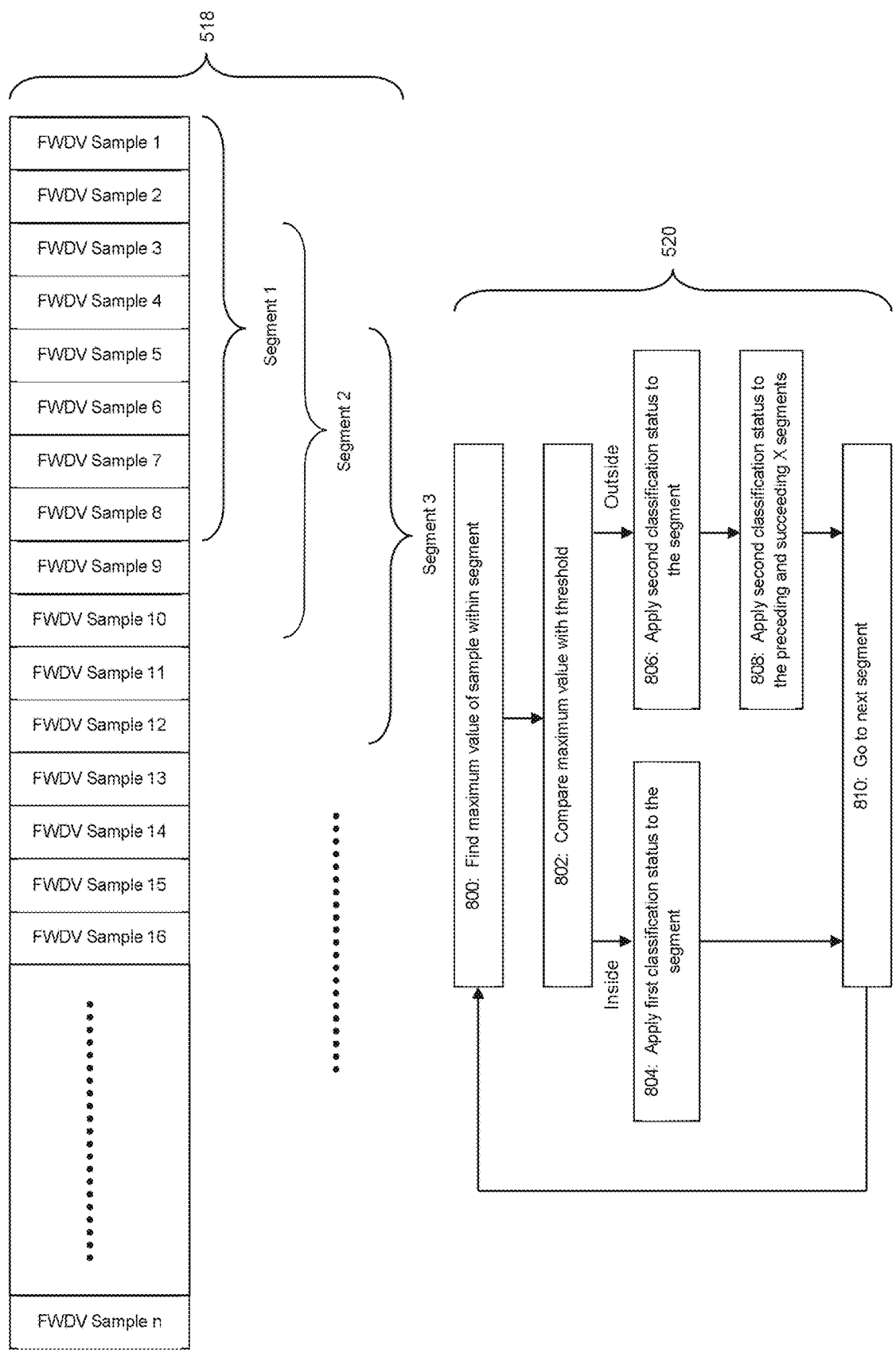
FIG. 8 shows an exemplary technique for segment validation.

Returning to FIG. 5, at step 516, the processor extracts a number of segments from the FWDV samples. For example, a 10 second sliding window with a 9 second overlap between segments can be employed to generate each segment. It is believed that such 10 second segments provide sufficient redundancy (beats within a segment) to minimize error while remaining small enough to permit an assumption of a stationary signal. The output of this step is thus a number of segments, each segment comprising a plurality of the FWDV samples, as shown in FIG. 8. It should also be understood that segment size need not be 10 seconds (for example, 5 second segments or 15 second segments could be used). Furthermore, it should be understood that non-overlapping segments could also be used.

At steps 520i (see steps 520a, 520b, ..., 520n in FIG. 5), the processor validates the segments according to defined criteria. These steps can thus assign classifications to each segment that contribute to the extraction of heart rate data. Furthermore, this classification can also contribute to the generation of data indicative of the person's restlessness, as explained below.

FIG. 8 illustrates an exemplary process flow for steps 520i. Due to high amplitude noise (e.g., body motion artifacts), there are some segments 518 from which heartbeat (and thus heart rate) cannot be reliably extracted. Thus, at step 800, the processor finds a maximum value among the samples within a segment. At step 802, the processor compares this maximum value with a threshold (e.g., 0.05 volts). If the maximum value is at or below this threshold, it is assigned a first classification status (step 804) that identifies the segment as usable to extract heart rate data. If the maximum value exceeds the threshold, it is assigned a second classification status (step 806) that identifies the segment as unusable to extract heart rate data. For such a segment deemed unusable, the corresponding heart rate for the segment can be set equal to zero or some other arbitrary value. Furthermore, to reduce the chance of error near such transient segments, the processor at step 808 can also apply this second classification status to a certain number of preceding and succeeding segments (e.g., the segments corresponding to 5 seconds before and after the unusable segment). Furthermore, the inventors notes that the second classification status can also be used to indicate the periods of time for bed restlessness, which can be another important parameter characterizing a person's sleep and health condition. At step 810, the processor proceeds to the next segment and returns to step 800. Further still, a practitioner may choose to analyze the segments deemed unusable to extract heart rate data to assess whether these segments are indicative of either restlessness (high amplitude noise) or a "not in bed" condition (a virtually flat signal). Further still, the segments can be analyzed to assess conditions such as the expected relative position on the bed (left side, right side, center, toward head or toward foot, etc.) of the subject or relative posture on the bed of the subject (on back, on side, etc.). It is expected that the segments will exhibit certain detectable patterns corresponding to such positions and postures that will permit estimation of these conditions.

Figure 9:
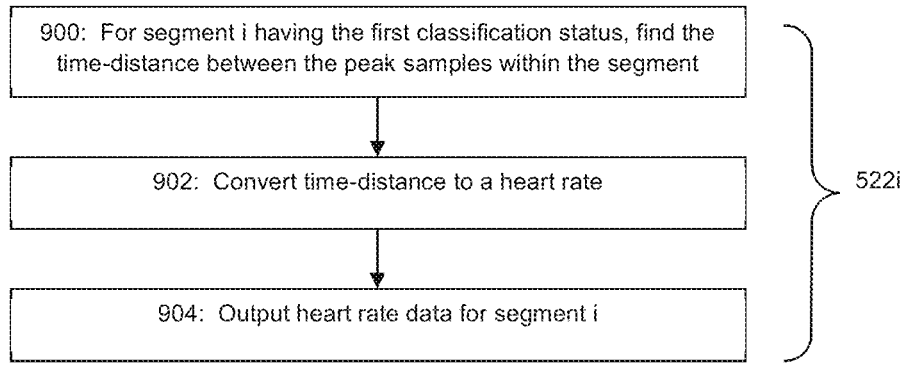
FIG. 9 shows an exemplary technique for determining a heartbeat rate from validated segments.

Returning to FIG. 5, at steps 522i (see steps 522a, 522b, ..., 522n in FIG. 5), the processor is then able to determine a heartbeat rate for each segment having the assigned first classification status. FIG. 9 illustrates an exemplary process flow for determining the heart rate of each segment having the first classification status. At step 900, the processor finds the time-distance between the peak samples within the segment. Autocorrelation may be used to perform step 900 to better reject the effects of a sudden change in heart rate or a momentary arrhythmia, although it should be understood that other techniques, such as calculating mean distance between peaks in the segment) could be employed. At step 902, this time-distance is converted to a heart rate to generate the output heart rate for that segment (step 904).

Returning to FIG. 5, the processor next performs averaging over the output heart rates for multiple segments (step 524). For example, the processor can average the heart rates over 6 segments. In accordance with the exemplary embodiment described herein, 6 segments would correspond to 15 seconds of the original data, which would be consistent with the clinical practice of counting beats over 15 seconds and multiplying by 4 (yielding beats per minute (bpm). The smoothing provided by step 524 is expected to reduce spurious error in calculating the heart rate from the hydraulic transducer, and the inventors deem averaging over time appropriate given the assumption of a stationary signal over a short duration.

Thus, through the process flow of FIG. 5, the system is able to extract heart rate data for a person from the sensor signal produced by a hydraulic sensor 102 as a person sleeps or rests in bed. The heart rate data generated by step 524 can be time-stamped and stored in a data structure in a database for subsequent analysis to assess a person's health condition. Moreover, as noted above, this process flow can also generate time-stamped data indicative of a person's restlessness for storage in a data structure in a database. This restlessness data can also be leveraged for subsequent analysis to assess a person's health condition. The database can be co-resident with processor 104 and memory 106 or it can be remote. Wired and/or wireless connections can be used to transmit the data to the database.

Figure 22:
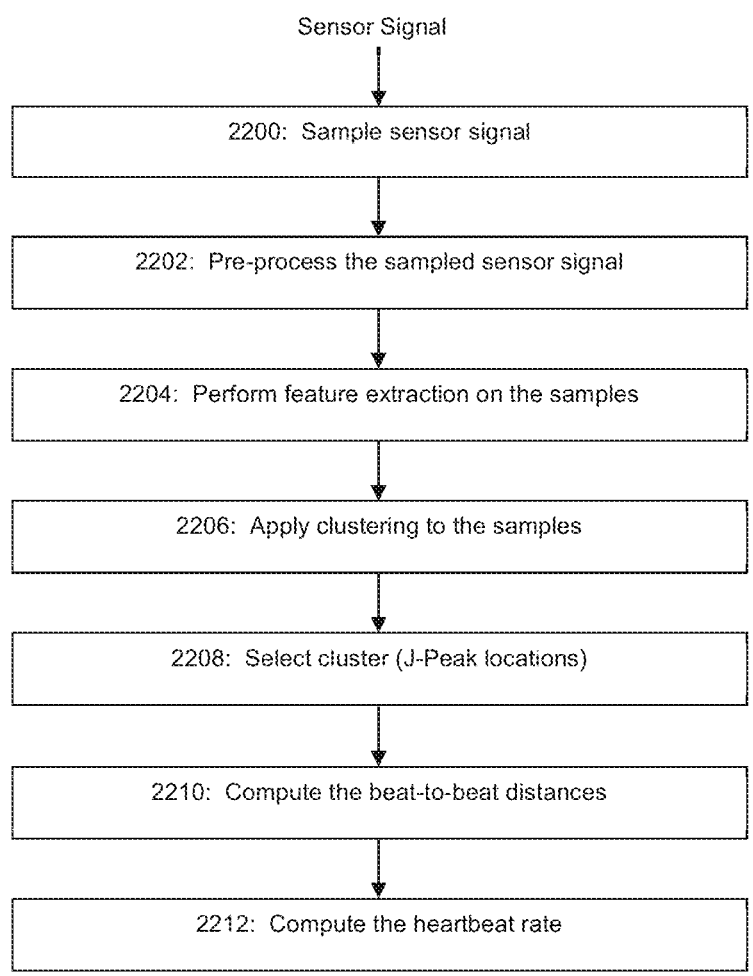
FIG. 22 shows an exemplary process flow for extracting heartbeat data from a sensor signal using a clustering analysis.

FIG. 22 illustrates an exemplary process flow for the processor 104 and memory 106 to extract heart rate data from the sensor signal using a clustering analysis. With the clustering analysis, the processor seeks to separate data corresponding to the sensor signal into multiple clusters based on various criteria that are pertinent to the signal for which extraction is desired, where at least one of these clusters is then selected for further processing to extract the desired information. In an exemplary embodiment, the clustering analysis can be deployed to group analyze the data into prospective J-peaks, and then group the prospective J-peaks into clusters based on criteria. The cluster deemed most likely to correspond to the J-peaks is then selected for use in computing the heart beat data.

At step 2200, the sensor signal is sampled. This step may operate as previously described with reference to step 500 of FIG. 5. Next, the sampled signal is pre-processed at step 2202. This pre-processing step may employ bandpass filtering to remove low frequency respiratory components of the signal. An exemplary bandpass range can be between approximately 0.4 Hz and 10 Hz. Additionally, an 8-point moving-average filter can be used to smooth the signal.

Figure 23:
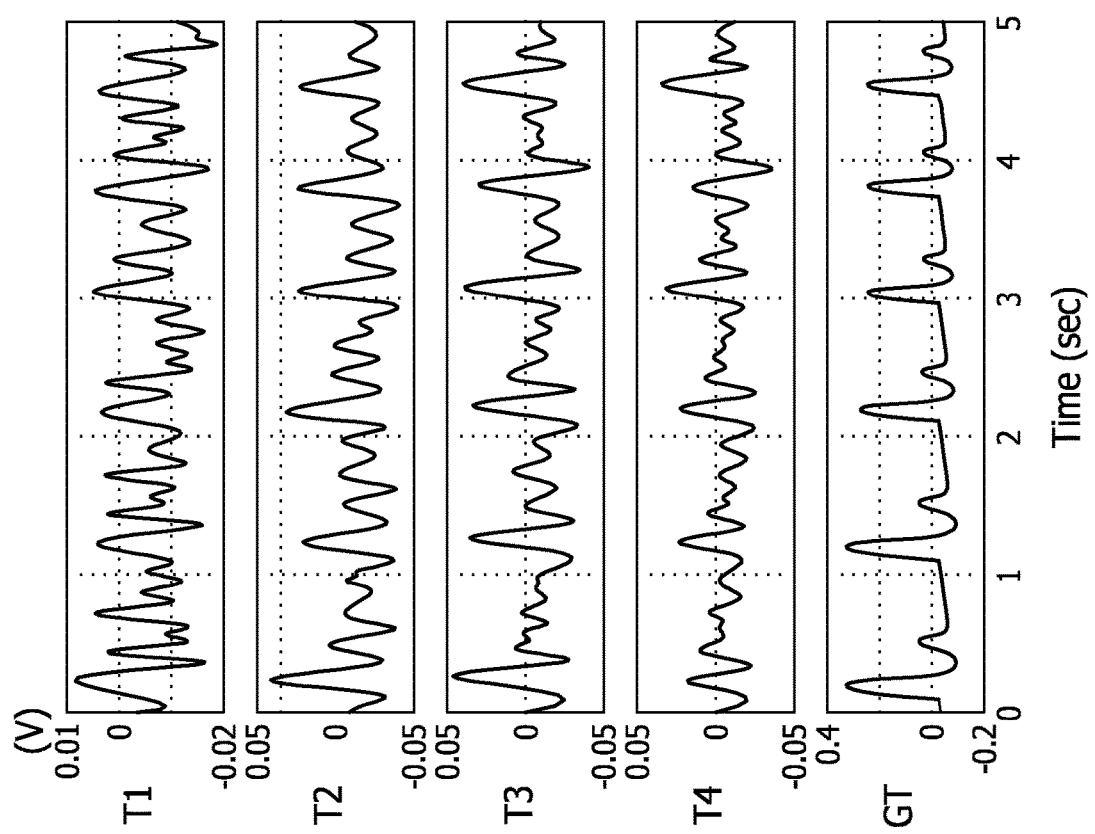
FIG. 23 shows BCG signals corresponding to various hydraulic transducers in a multi-transducer arrangement, together with a ground truth reference.
Figure 24:
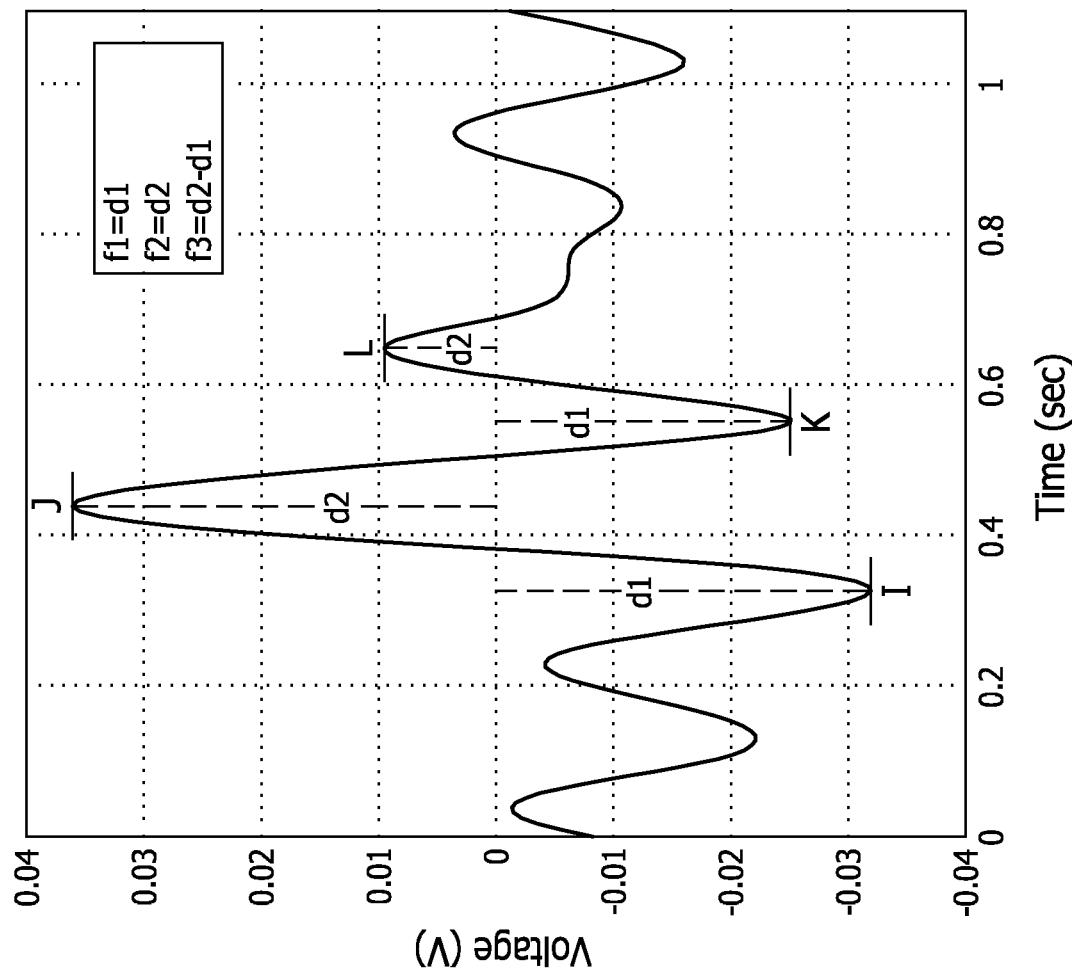
FIG. 24 shows exemplary features that can be extracted from a BCG signal.
Figure 29:
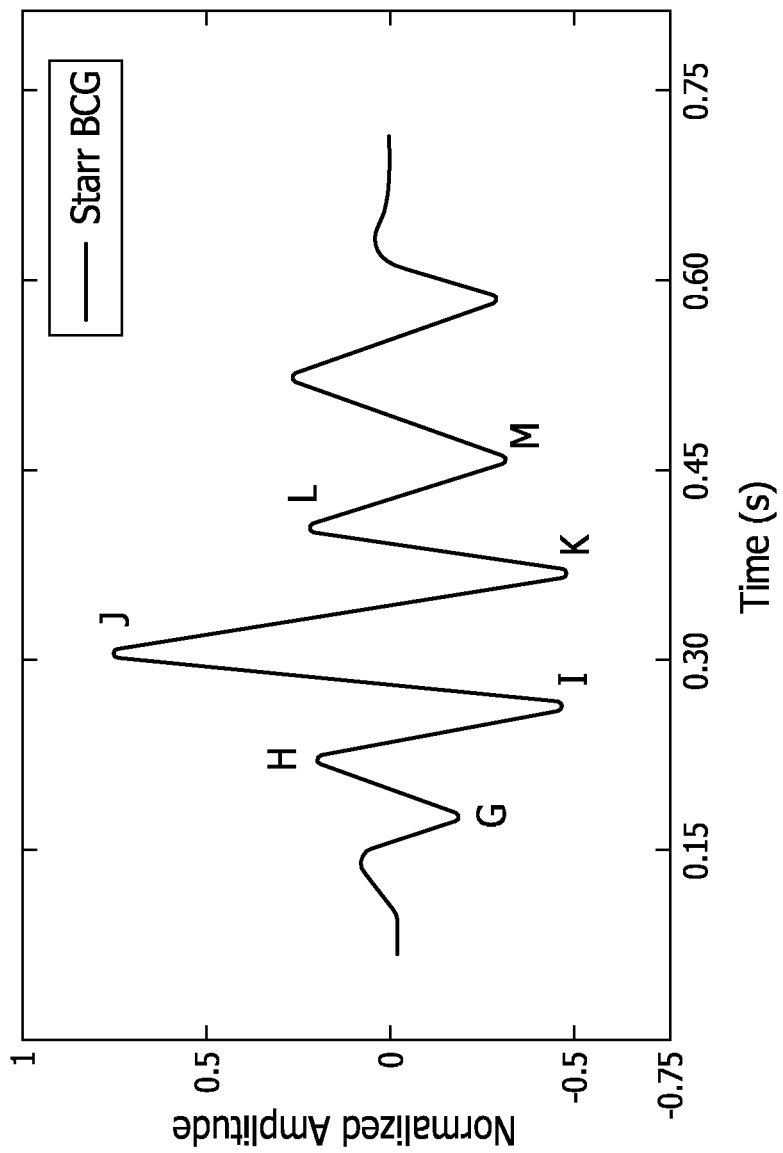
FIG. 29 shows an exemplary BCG signal portion.

At step 2204, the processor performs feature extraction on the pre-processed samples. The BCG signal captured by the sensor 102 will show the occurrence of heartbeats for one or more hydraulic transducers. For example, FIG. 23 shows exemplary 5-second segments of BCG signals captured for a subject by 4 hydraulic transducers T1-T4 in accordance with the exemplary hydraulic sensor embodiment of FIG. 3 (where the bottom row shows the ground truth signal from a finger sensor worn by the subject). For convenience, one can assume that the beginning of an individual heartbeat is represented by the J-peak (see FIG. 29). However, as can be seen in FIG. 23, for sufficiently short window lengths, multiple peaks are present in the signal, and not all of these peaks will correspond to J-peaks. Thus, further analysis is needed to assess which of the peaks are the most likely ones to be J-peaks. The feature extraction of step 2204 facilitates this analysis by computing various features for each prospective or candidate J-peak (where such prospective/candidate J-peaks may include L peaks for example). It should also be understood that the BCG signal captures by the hydraulic sensor will not exhibit a self-repeating pattern for the peaks that are around the J-peak due to the presence of movement, respiration, or the system itself. As an additional noise reduction, step 2204 can characterize only the J-peak and adjacent valley. With reference to FIG. 24, features that can be extracted from the signal include features f1, f2, and f3 for each and every local maxima and minima in the filtered signal data, where:

f1 is computed as the distance from zero to depletion (see depletions d1 to I and K as shown in FIG. 24.

f2 is computed as the distance from zero to peak (see peaks d2 to J and L as shown in FIG. 24.

f3 is computed as the summation of d1 and d2 for each segment, as shown in FIG. 24 (where it is assumed the d1 value will be a negative number).

However, it should be understood that other features pertinent to J-peak detection could be extracted at step 2204. Furthermore, to detect the local maxima and minima for computing f1, f2, and f3, windowing can be used to group samples into segments (e.g., segments of 5-15 seconds although other values could be used), where the maximum and minimum in each window are found. However, it should be understood that other techniques could be used to find the local maxima and minima. For example, the inflection points in the general trajectory of the waveform defined by the samples can be captured as local maxima/minima.

At step 2206, the processor applies a clustering analysis to the extracted features for each segment to group the prospective/candidate J-peaks in 3-D space, where each dimension corresponds to a different one of the three features f1-f3. In an exemplary embodiment, the clustering analysis can be a k-means clustering analysis. Further, a random initialization of the centers can be used. The number of centers was selected as two, under the assumption that one of them will contain the J-peaks and the other will group the rest of the peaks. Because it is expected that most of the prospective J-peaks will actually not be J-peaks, the smallest cluster is assigned to the "heartbeat class" (HB) and the larger cluster is assigned to the "non-heartbeat class" (NHB).

K-means clustering aims to partition N observations into k clusters in which each observation belongs to the cluster with the nearest mean. K-means clustering can be viewed as a special case of the generalized hard clustering algorithm scheme when point representatives are used and the squared Euclidean distance is adopted to measure the dissimilarity between vectors $x_i$ and representatives $\theta_j$, where $\theta_j$ is the mean of cluster j and where $x_i$ is the i-th point of the dataset X, for i=1, . . . , N.

The k-means algorithm is derived by minimizing a cost function of the form:

$$J(\theta,r)=\Sigma_{i=1}^{N}\Sigma_{i=1}^{K}r_{ik}\|x_i-u_k\|^2$$

with respect to $r_{ik}$ and $u_k$, where $X=\{x_i, \ldots, x_N\}$ describe the dataset (the set of data for the prospective/candidate J-peaks), $r_{ik}$ is the set of binary indicator variables in [0,1] to indicate membership in one of the clusters, and k=1, . . . , m describe which of the K clusters the data point $x_n$ is assigned to, so that if data point $x_i$ is assigned to cluster k, then $r_{ik}=1$.

An exemplary pseudo-code for the application of the k-means algorithm at step 2206 can be:

Choose arbitrary initial estimates for $u_k(0)$ for the $u_k$, k=1, . . . , m
Repeat
  For i=1 to N
    Determine the closest representative $u_k$, for $x_i$. Compute $r_{ik}$
    Set b(i)=k.
  End (For-i)
  For j=1 to m
    Parameter updating: Determine $u_k$, as the mean of the vectors $x_i$ belongs to X with b(i)=k.
  End (For-j).
Until no change in the $u_k$'s occur between two successive iterations.

Note that $\theta_j$ is the parameterized representative (mean) of the j-th cluster, $\theta_j=[, \ldots, \theta_m]$, b is a label vector, and m is the number of clusters.

At step 2208, the processor selects the cluster that contains the J-peak locations. The results of the k-means processing at step 2206 are stored in two vectors, each vector corresponding to a different one of the two clusters. As noted above, this cluster is expected to be the smaller cluster of the two.

Next, at step 2210, the processor computes the beat-to-beat distances for the J-peak locations from the selected cluster, and at step 2212, the processor computers the heartbeat rate. The processor may use the techniques described above in connection with FIG. 5 for these operations.

Extracting Respiratory Information from the Sensor Signal

Figure 10:
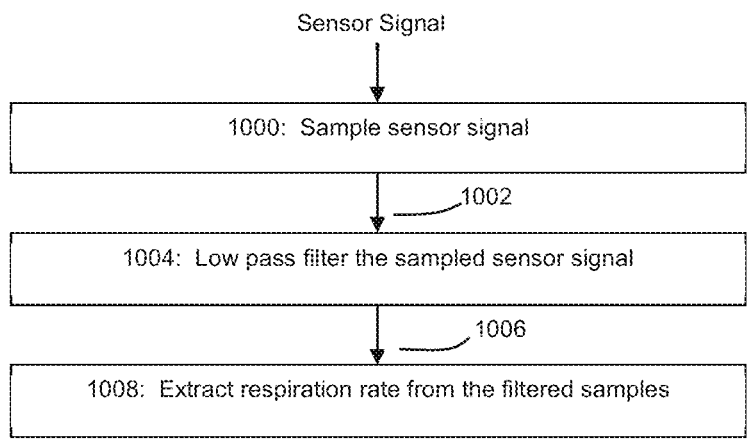
FIGS. 10-11 show an exemplary technique for extracting respiratory date from a sensor signal.
Figure 11:
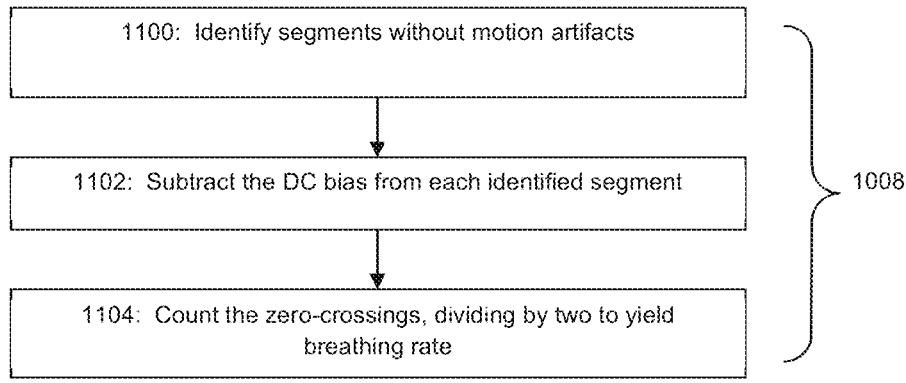

Another item of physiological data that can be extracted from the sensor signal 108 is a person's respiratory rate. The respiratory component in the sensor signal 108 is of much lower frequency, has smoother transitions, and has greater amplitude than either the cardiac component or the noise component. Thus, relative to extracting the heart rate, extracting the respiratory rate for a person from the sensor signal 108 is an easier task. Respiration can readily be detected from sensor signal 108 via low pass filtering. The general process for extracting the respiratory component is illustrated in FIG. 10 and explained step-by-step as follows. At step 1000, the sensor signal is sampled to generate a plurality of samples 1002. This operation can be the same as described above for step 500. Then, the processor can low pass filter the samples using a low pass filter with a cutoff frequency ranging from around 1-4 Hz to yield filtered signal 1006. To extract the respiratory rate (step 1008), the processor can, as shown in FIG. 11, identify 1-minute segments within the signal 1006 without motion artifacts (step 1100), subtract the DC bias from each segment (step 1102), and determine the breathing rate by counting the zero-crossings and dividing by two (step 1104). This approach is expected to readily detect the rate of normal respiration as well as conditions such as apnea. Furthermore, it should be understood that the process flows of FIGS. 10 and 11 are exemplary only and other techniques could be employed to extract the respiratory component of the sensor signal.

Figure 13:
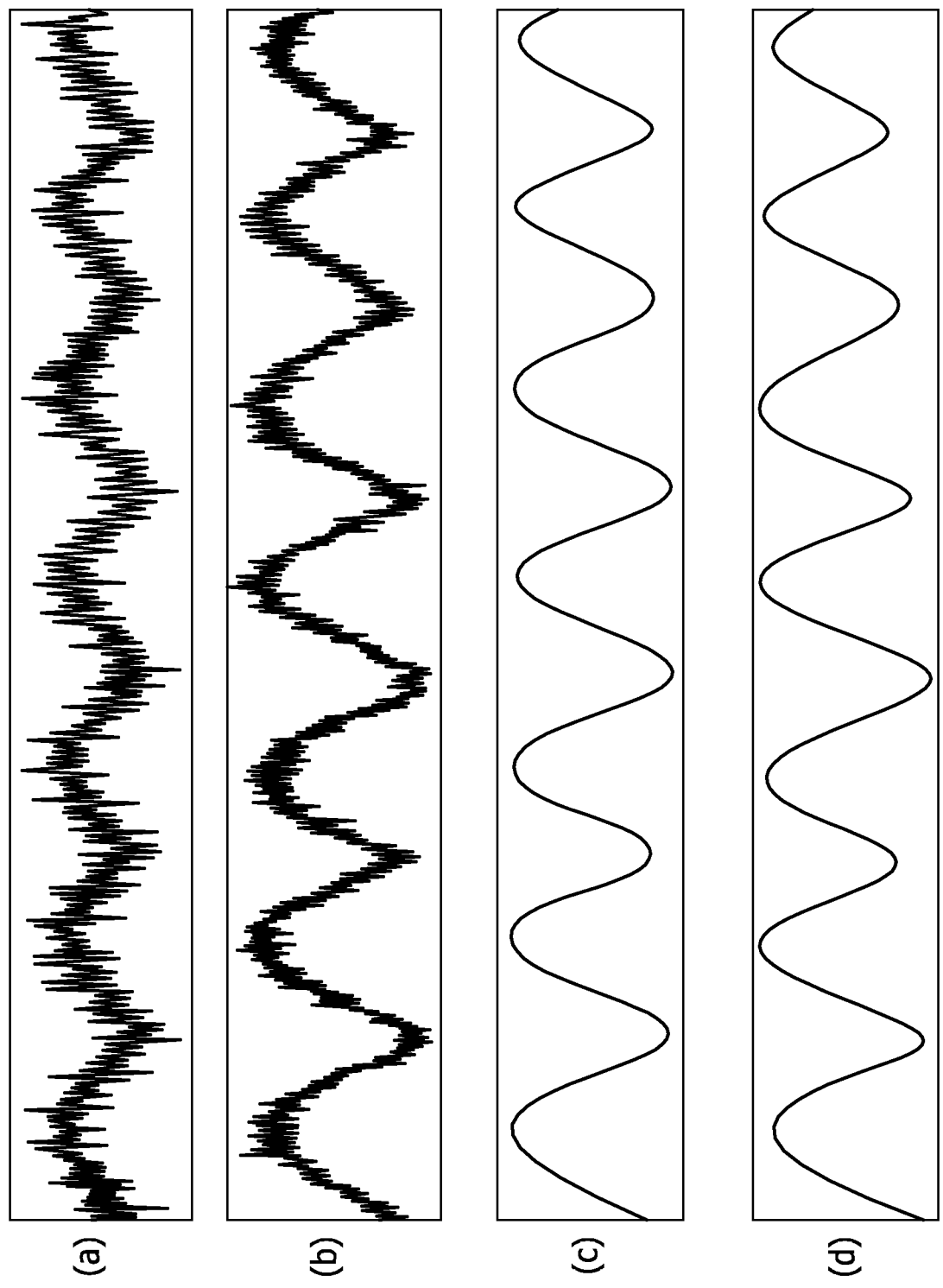
FIG. 13 shows exemplary signals at various stages of the process flow for the respiratory information extraction algorithm of FIG. 10.

FIG. 13 shows that the process flow of FIG. 10 can clearly extract the respiratory component of the sensor signal 108.

FIG. 13(a) shows the sensor signal 108 over a 30 second segment. FIG. 13(b) shows the reference ground truth from a piezoelectric respiratory band worn around the torso over the same segment of time. FIGS. 13(c) and (d) show the signals of FIGS. 13(a) and (b) (respectively) after low-pass filtering with 1 Hz cutoff frequency. The respiration is clearly evident in FIG. 13(c) with a high degree of correlation relative to the reference of FIG. 13(d).

Thus, through the process flow of FIG. 10, the system is able to extract respiratory rate data for a person from the sensor signal produced by a hydraulic sensor 102 as a person sleeps or rests in bed. The respiratory rate data generated by step 1008 can be time-stamped and stored in a data structure in a database for subsequent analysis to assess a person's health condition.

In comparing sensor data changes to health changes, a bed sensor has proven to be a useful component of the sensor network. Observation of bed sensor data has revealed instances of dramatic changes over a very short time, as well as more gradual changes over 2-3 weeks, that correspond to impending changes in health condition, e.g., cardiac problems. Thus, research has shown the importance of this type of continuous monitoring in the home setting.

Thus, a processor can analyze the database of heart rate data, respiratory rate data, and restlessness data to assess a person's health condition. Over time, patterns in a person's heart rate, breathing, and restlessness can be quantified to make judgments about health. Further still, the database records can be categorized to provide further health insights. For example, a person's heart rate can be identified as "low" (e.g., if the extracted heart rate is below 40 beats per minute), "normal", or "high" (if the extracted heart rate is greater than 100 beats per minute). However, it should be understood that other values for separating the categories could be used, as could additional or different categories. Similarly, a person's respiratory rate can be identified as "low" (if the extracted respiratory rate is less than 7 breaths per minute), "normal", or "high" (if the extracted respiratory rate is greater than 31 breaths per minute). However, once again, it should be understood that other values for separating these categories could be used, as could additional or different categories. As another example, restlessness can be categorized to one or more possible levels depending on the time of continuous movement identified by the "unusable" segments from the process flow of FIG. 5.

Figure 14:
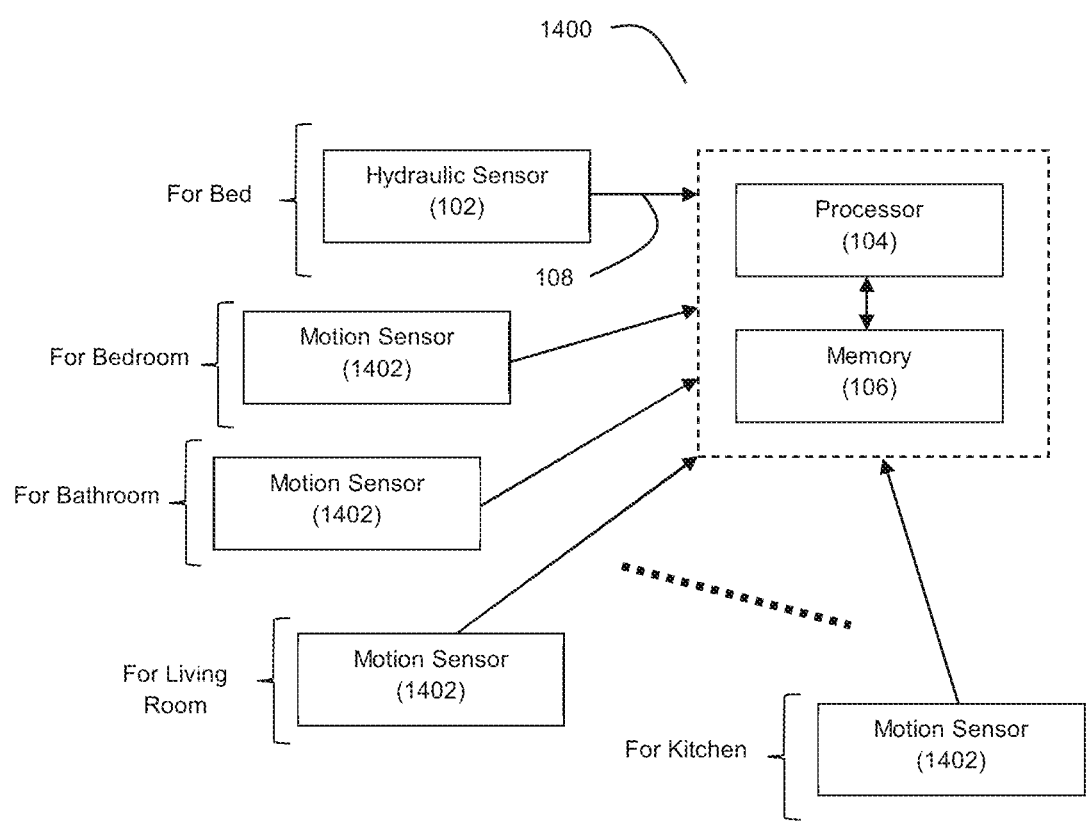
FIG. 14 shows an exemplary sensor network including a hydraulic sensor and other sensors.

Further still, the inventors note that the system 100 including the hydraulic sensor 102 can be employed as a bed sensor within an integrated sensor network 1400 for a person's living space as shown in FIG. 14. An example of a suitable sensor network is described in U.S. Pat. App. Pub. 2010/0302043, the entire disclosure of which is incorporated herein by reference. Thus, the hydraulic bed sensor 102 could be used in conjunction with other types of sensors such as motion sensors 1402 and the like to track a person's health. Motion sensors can be used to detect instances of falls or motionlessness by a person in various areas of a person's living space while the hydraulic sensor 102 can be used to detect smaller scale physiological conditions for the person while in bed, such as heartbeat, respiration, and restlessness as explained herein. It should be understood that the processor 104 and memory 106 shown in FIG. 14 may comprise a plurality of processors and memories if desired by a practitioner.

Signal Selection

Figure 25:
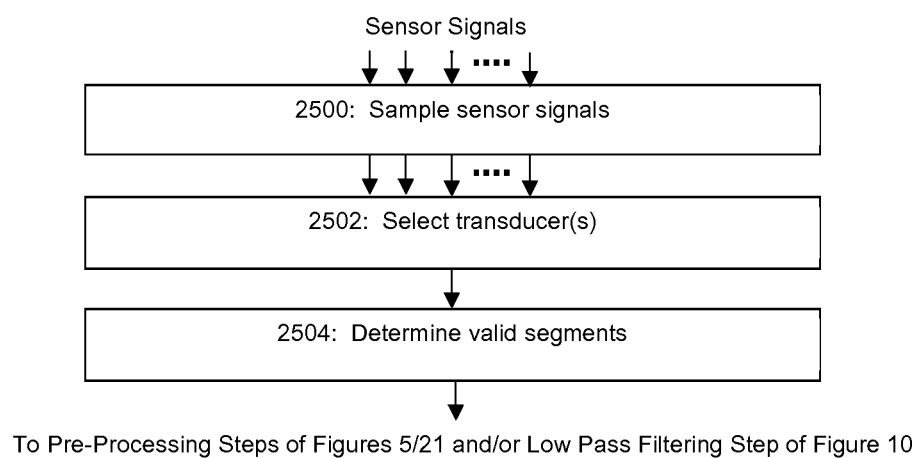
FIG. 25 shows an exemplary process flow for selecting from among the sensor signals corresponding to multiple hydraulic transducers.

In embodiments where multiple hydraulic transducers 200 are deployed, a practitioner may want to employ logic to determine which of the sensor signals will be further processed to extract the desired physiological data. Toward this end, FIG. 25 discloses an embodiment wherein the outputs of the various hydraulic sensors 102 are analyzed to decide which of the sensor signals to use as the source for the physiological data extraction.

At step 2500, the sensor signals corresponding to the various hydraulic transducers 200 are sampled. This sampling may proceed as described in connection with step 500 of FIG. 5. Next, at step 2502, the processor selects at least one of hydraulic transducers 200 that will be used as the source for the sensor signal(s). As an example, to do so, the processor can select the sensor signals whose voltage levels exceed a threshold voltage. This threshold voltage can be set to equal or approximate the voltages recorded by the hydraulic sensors 102 when no one is lying on the bed. If desired, a practitioner can set this threshold voltage independently for each of the hydraulic sensors 102 based on the voltage outputs of each sensor 102 when no one is lying on the bed. Each sensor signal passing this threshold can be selected at step 2500, or a practitioner can select only a subset of the sensor signals passing threshold, depending on the desires of a practitioner (for example, selecting the two sensor signals with the highest voltage magnitudes from among the sensor signals passing the threshold).

At step 2504, the processor then determines the valid segments of the selected sensor signal(s). These valid segments are then further processed to extract the relevant physiological data (e.g., to the pre-processing steps of FIGS. 5 and/or 21 for extracting heartbeat data and/or the low pass filtering step of FIG. 10 for extracting respiratory information). To determine which segments of the selected sensor signal(s), the processor can compute a reference standard deviation of voltage values for the selected sensor signal(s) or a portion thereof (e.g., using a sliding window of the selected sensor signal(s)). This can be done on a per selected sensor signal basis if desired. This reference standard deviation could then be used to evaluate the selected sensor signal(s) over defined intervals (e.g., every five seconds) for thresholds of ±1*std. Thus, the segments of the selected sensor signal(s) (e.g., 5-second segments) whose standard deviations are within ±1*std of the reference standard deviation for that selected sensor signal are identified as valid and passed along for further processing.

It should be further understood that a practitioner may choose to simply extract the desired physiological information from all of the hydraulic sensors 102. In such an embodiment, a practitioner may also choose to compute an average of the resulting extracted item of physiological data (e.g., a mean or median of the extracted physiological information from each of the hydraulic sensors).

Experimental Results

WPPD Analysis

A. Methodology

Figure 15:
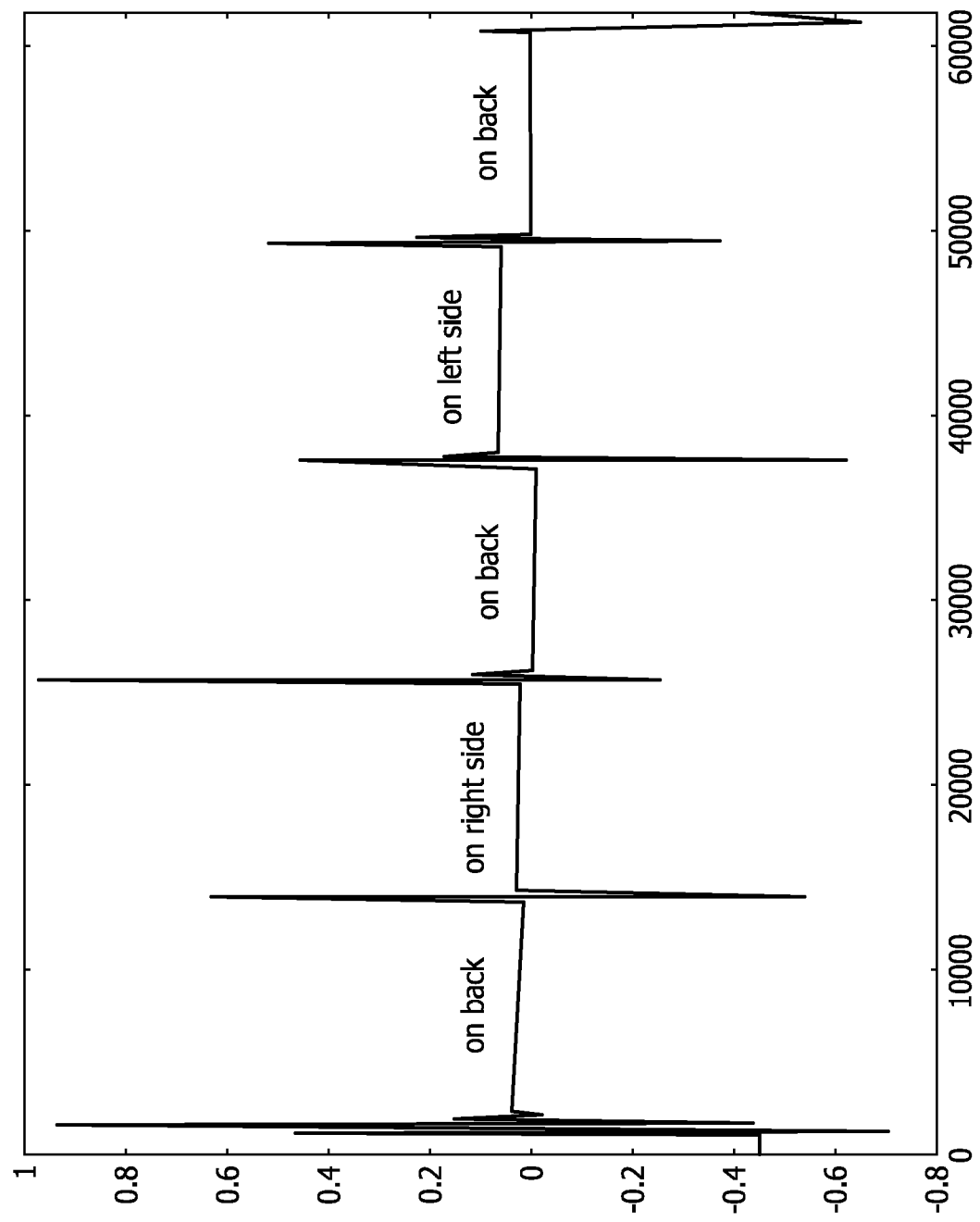
FIG. 15 shows data from a hydraulic bed sensor after initial filtering and downsampling.

To test a prototype hydraulic bed sensor, preliminary data were collected from two subjects, one male and one female. Subjects were asked to lie on the bed for approximately 10 minutes, following the pattern of on the back, on the right side, on the back again, on the left side, and on the back once more (with approximately two minutes in each position). This process was performed twice for each subject, once with the hydraulic transducer on top of the mattress (beneath the linens), and once with the hydraulic transducer underneath the mattress. Subjects were not told to lie "perfectly still," but instead were asked to lie as though they were at rest and move from position to position as they might while sleeping. Data were collected continuously during this period without any denotation of changes in position. As can be seen in FIG. 15, the position changes are evident in the recorded data.

FIG. 15 shows data from the hydraulic bed sensor after initial filtering and downsampling to 100 Hz. The y-axis units are in volts; the x-axis units are in samples (100 samples per second). The transients indicate bed motion, while the relatively flat sections show the subject following the pattern of the experiment (back, left side, back, right side, back). The difference in static pressure is evident between lying on the back and lying on the side.

To provide ground truth for validating the hydraulic sensor, data were collected simultaneously from a pulse sensor connected to the subject's finger and a respiration band wrapped around the subject's torso. Both the pulse and respiratory sensors use piezoelectric sensors, giving artifacts of motion when the subject moves from position to position. This ground truth is used as the baseline for evaluating the effectiveness of the hydraulic sensor. The section below reports the pulse rate results.

B. Results

Figure 16:
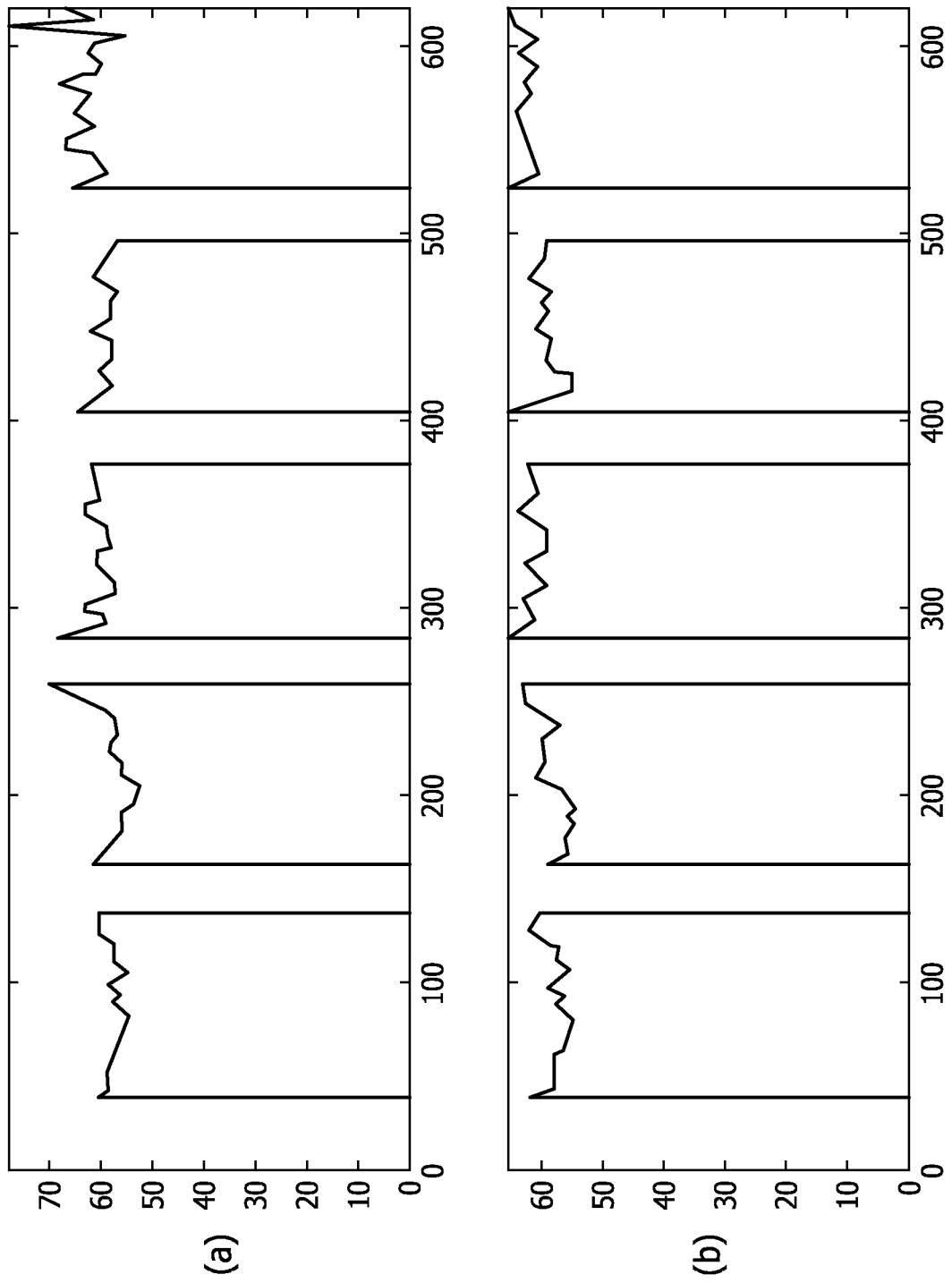
FIG. 16 shows an extracted heart rate for a female subject with a hydraulic sensor beneath a mattress.

Visual inspection of heart rates extracted from the hydraulic sensor show a strong correlation with heart rates extracted from the piezoelectric pulse transducer worn on the finger. For further comparison, heart rates were automatically extracted from the pulse transducer using the same method as the hydraulic transducer, except that the segment validity threshold was raised to 0.5 (given the much higher signal-to-noise ratio of the pulse transducer). A sample comparison is shown in FIG. 16, excluding segments deemed unusable due to motion.

FIGS. 16(a) and (b) show extracted heart rate from the female subject, with hydraulic sensor beneath mattress; FIG. 16(a) shows the heart rate extracted from the hydraulic sensor, while FIG. 16(b) shows the heart rate extracted from the piezoelectric pulse transducer worn on the finger. Y-axis units are in beats per minute (bpm); x-axis units are in seconds.

A method to compare the extracted heart rates quantitatively was also developed, yielding:
the average difference, in bpm, between the hydraulic transducer and the piezoelectric pulse transducer, and
the percentage of segments for which the heart rate extracted from the hydraulic transducer was within 10% of the rate extracted from the piezoelectric pulse transducer.

The justification for using a benchmark of 10% from ground truth is practical; reporting heart rates accurate within 10% is sufficient for the types of analysis and diagnosis envisioned for a system. As explained in connection with FIG. 5, the heart rate detection algorithm will give an estimated heart rate for each second of the input signal. Thus, the experimental results are evaluated on a second-by-second basis.

The results are summarized in Table 1, showing the accuracy of the hydraulic sensor relative to the piezoelectric pulse sensor over approximately 600 seconds of data (thus, comparing approximately 600 individual data points) for each run. Additionally, Table 2 and Table 3 show the results for each position (approximately 120 seconds each) during the data runs where the sensor was positioned underneath the mattress.

TABLE 1

Experimental Results of Extracting Pulse Rate

| Experimental Run | Average Difference in Beats per Minute | Percentage of Time Hydraulic Sensor was Within 10% |
|---|---|---|
| Female, sensor on bottom | 1.34 | 98.9 |
| Male, sensor on bottom | 2.95 | 92.5 |
| Male, sensor on top | 6.70 | 70.2 |
| Female, sensor on top | 13.4 | 52.6 |

TABLE 2

Results for Each Position, Female Subject, Sensor on Bottom

| Female, on back #1 | 0.49 | 100 |
|---|---|---|
| Female, on right side | 2.12 | 100 |
| Female, on back #2 | 0.69 | 100 |
| Female, on left side | 1.22 | 100 |
| Female, on back #3 | 2.16 | 94.8 |

TABLE 3

Results for Each Position, Male Subject, Sensor on Bottom

| Male, on back #1 | 3.60 | 89.4 |
|---|---|---|
| Male, on right side | 5.82 | 72.6 |
| Male, on back #2 | 1.22 | 100 |
| Male, on left side | 2.28 | 100 |
| Male, on back #3 | 1.57 | 100 |

The results indicate that the hydraulic bed sensor is effective at extracting heart rate when the transducer is positioned beneath the bed mattress. It should be noted that these results are statistically consistent with the ground truth; a t-test of the results from the hydraulic transducer placed below the mattress did not indicate a significant difference from the piezoelectric pulse transducer (ground truth) at the 5% level, for either the male or female subjects. (The t-test did indicate significant difference from ground truth for the hydraulic transducer placed above the mattress.) The increased accuracy of the system with the transducer below the mattress compared to on top seems to be due to the buffering effect of the mattress itself, as it seems to filter some of the erratic artifacts from small movements of the body while at rest. The constant weight of the mattress on the transducer also adds stability to the fluid within the sensor. Also, significantly, the orientation on the bed (on back, on side) does not seem to affect sensor reliability.

Ground Truth Acquisition

Ground truth for validating the output of the hydraulic sensor is collected via a piezoelectric pulse sensor connected to the subject's finger (ADInstruments MLT1010) and a piezoelectric respiration band wrapped around the subject's torso (ADInstruments MLT1132). These signals are simultaneously acquired and sampled through the same ADC as the signal from the hydraulic sensor, using the same sampling rate and avoiding issues of synchronization between separate devices.

Evaluating the Robustness of the WPPD Extraction Algorithm

In order to evaluate the robustness of the WPPD extraction algorithm, the inventors generated synthetic signals, allowing explicit control of frequency and amplitude for both heartbeat and respiration. This approach was taken to provide a measure of confidence in the inventors' methods prior to embarking on a full study with human subjects.

Additionally, the inventors were interested in distinguishing shallow breathing from low heart rate, and would like to evaluate whether the extraction algorithm can handle such a scenario.

To generate synthetic signals, the inventors acquired a real signal through the system, separated and extracted the cardiac and respiratory components of the original composite signal, and then manipulated the individual components in isolation before recombining into new composites. One of the questions the inventors wished to address is whether the system is able to distinguish heartbeats in the presence of very high respiration rates; to address this, the inventors changed the rate and amplitude of the respiration component, recombined with the cardiac component, and then ran the heartbeat detection algorithm of FIG. 5.

Manipulating amplitude of the respiratory component is achieved by simply scaling the sample values by a chosen constant. Frequency is controlled by choosing a segment of respiration, resampling at a higher or lower rate to yield the desired change, and repeating the resampled segment (choosing appropriate zero-crossing endpoints to avoid discontinuities). The respiratory component of the signal is of low enough frequency that such a resampling does not result in any corruption of the original signal, and provides a realistic model of breathing output at the target frequency.

The inventors synthesized signals with respiration rates that are 0.5, 1, 2, 4, and 8 times the frequency of the actual respiration signal captured. The inventors have also scaled the amplitude of the respiration by factors of 0.25, 0.5, 1, 2, and 4, and added every possible respiratory combination with an extracted cardiac component. In every case, 100% heartbeat detection was achieved (36 out of 36 over a 30 second segment). An example of the synthesized signal along with the detected heartbeats (superimposed over the ground truth) is shown in FIG. 17.

Figure 17:
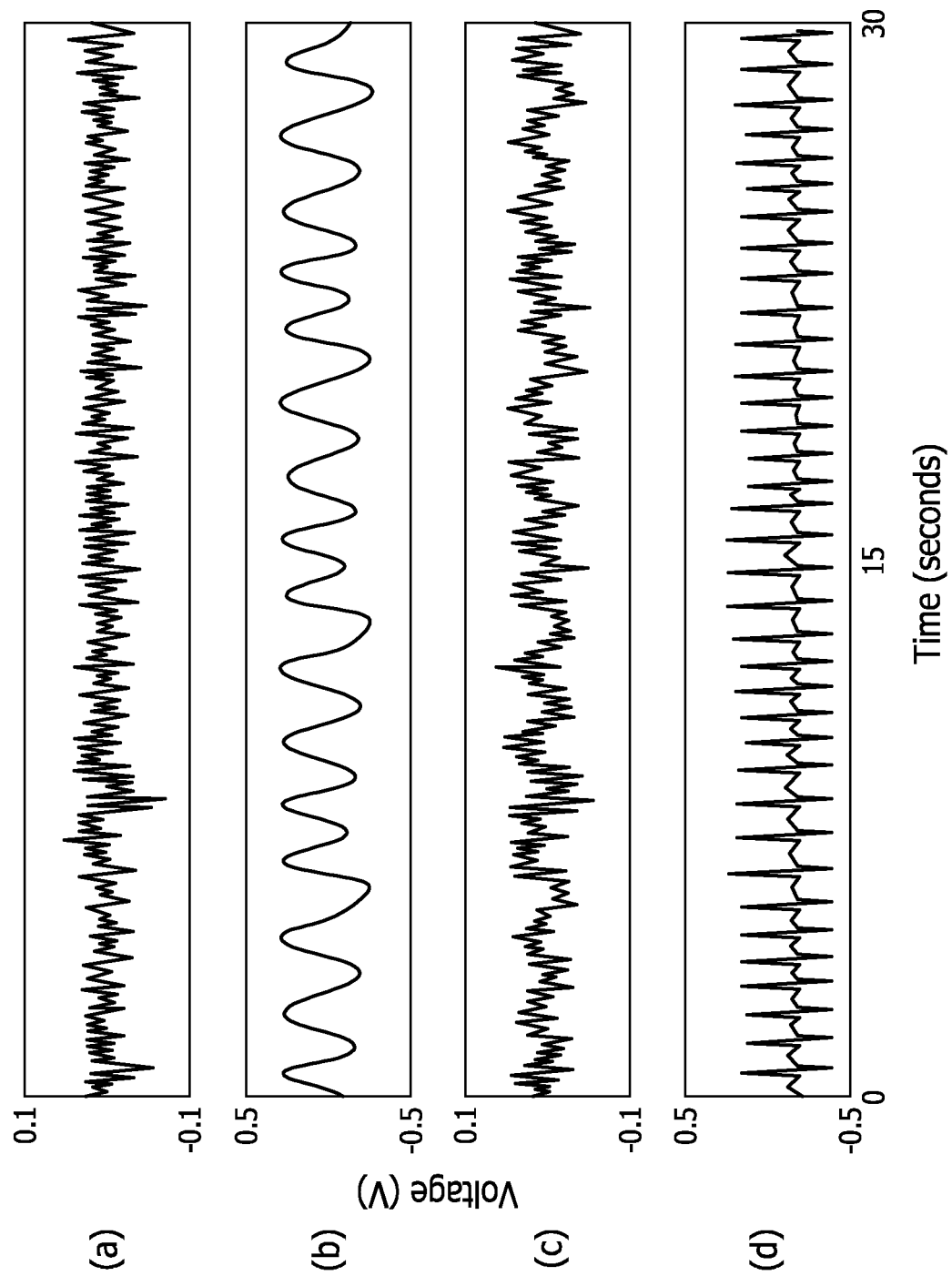
FIGS. 17-18 show various signals for evaluating robustness of the heartbeat extraction algorithm.

FIG. 17 shows heartbeats detected from synthesized signal. Specifically, FIG. 17(a) shows the cardiac component (extracted from real data), FIG. 17(b) shows the synthesized respiratory component (at 4 times the original captured frequency and the amplitude), FIG. 17(c) is the resulting composite (the inventors' synthesized signal), and FIG. 17(d) shows detection of heartbeats from the extraction algorithm compared to the ground truth.

To confirm the validity of this approach to synthesizing a signal, the inventors simulated similar conditions by having a subject breathe at a specified rate during data collection. The signals for a 30-second segment of this test are shown in FIG. 18.

Figure 18:
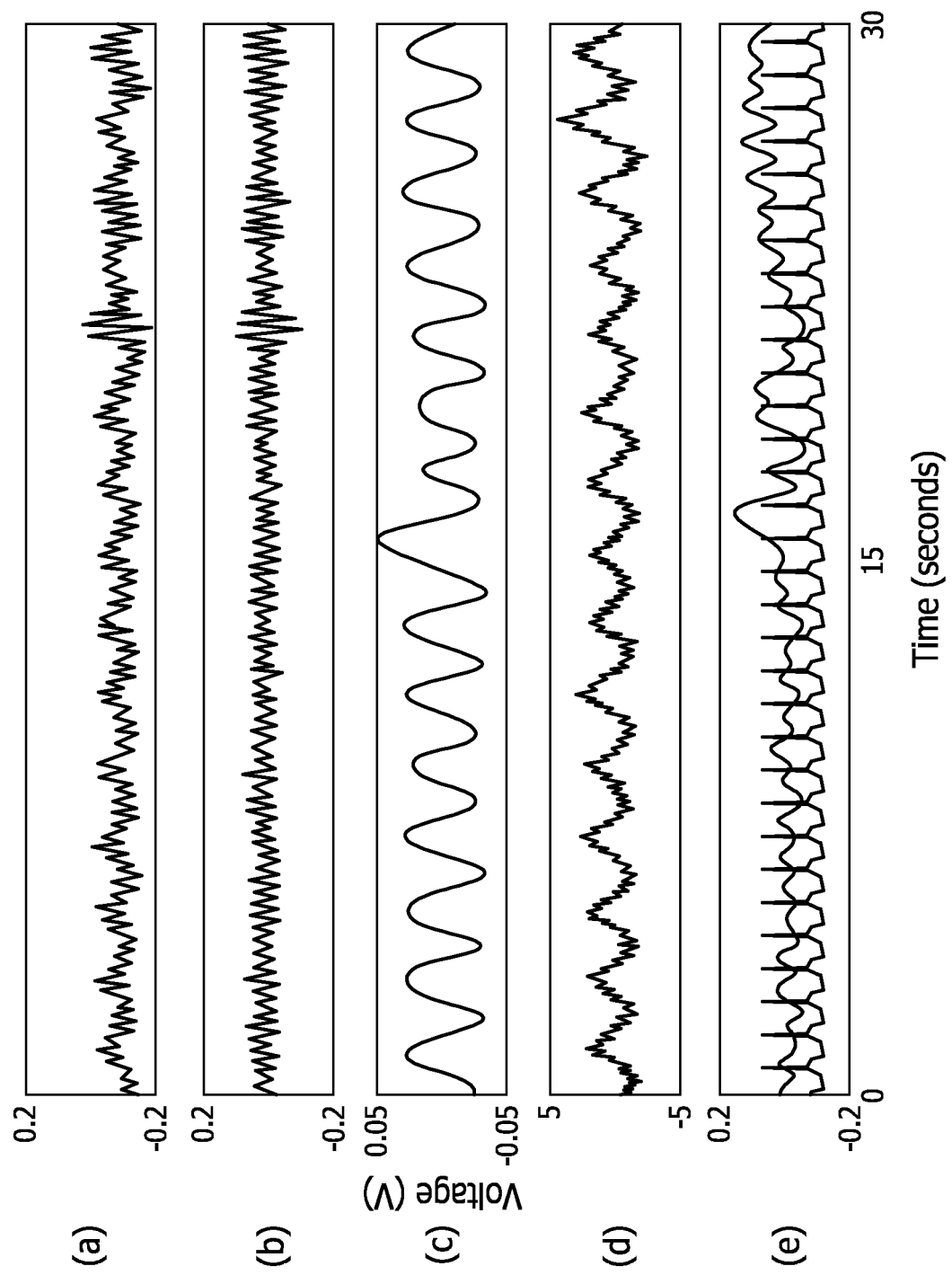

FIG. 18 shows the detection of heartbeats from real data. Here, the subject was asked to breathe at approximately 30 breaths per minute: FIG. 18(a) shows the collected signal, FIG. 18(b) shows the extracted cardiac component, FIG. 18(c) shows the extracted respiratory component, FIG. 18(d) shows the respiratory ground truth (from a piezoelectric respiratory belt), and FIG. 18(e) demonstrates identification of heartbeats by the hydraulic sensor and algorithm compared to the ground truth. Note that the algorithm detects heartbeats directly from the signal of FIG. 18(a); FIG. 18(b) is only shown for reference and comparison to FIG. 18(a).

The inventors thus conclude that the extraction algorithm for detecting heartbeats is relatively insensitive to changes in respiration, and there is very little chance of respiration being erroneously detected as low heart rate. Robustness of the heartbeat detection algorithm in the presence of varying respiration is expected due to the manner in which it operates. Specifically, since the WPPD analysis is effectively detecting a sudden increase (or impulse) of energy in the system within a small window, it should not be affected by respiration (because, even at 60 breaths per minute, respiration will not cause sudden impulses of energy since the lungs do not operate in a pulsatile fashion).

Evaluation Trial

After the inventors' preliminary testing of the system and evaluation of the extraction algorithm, the inventors further conducted a small trial involving five subjects, utilizing the second hydraulic transducer prototype described above (see Table 4 for summary information).

This group, while small, was representative of a wide range of ages, gender, body types, and cardiac conditions. This is significant, given that a target eldercare population is of advanced age, often with diagnosed cardiac problems. Two of the subjects reported prior cardiac conditions; one had a previously repaired ventricular septal defect, and another had suffered a mild heart attack.

TABLE 4

Details of Population for Evaluation Trial

| | Gender | Age | Weight (kg) | Height (cm) | Prior Cardiac History |
|---|---|---|---|---|---|
| Subject #1 | Male | 24 | 113 | 183 | No |
| Subject #2 | Male | 30 | 79 | 187 | No |
| Subject #3 | Female | 31 | 53 | 163 | Yes |
| Subject #4 | Female | 56 | 68 | 163 | No |
| Subject #5 | Male | 67 | 76 | 177 | Yes |

The subjects were asked to lie on the bed for periods of two minutes on the back, right side, back, left side, and back again (approximately 10 minutes in total). After collecting the data, the extraction algorithm of FIG. 5 was used to detect heart rates. Preliminary examination of these data led the inventors to modify two parameters of extraction algorithm: the size of the window, ws, used for the WPPD, and the cutoff frequency, f, used for post-WPPD low-pass filtering. Choices of ws included 150, 250, 400, and 600 ms; choices of f included 1, 1.5, and 2 Hz. FIG. 21 shows the results of this testing.

FIG. 21 indicates, for each subject, and for each combination of algorithm parameters (ws is the WPPD window size, f is the post-WPPD filter cutoff frequency), the percentage of 15-second segments for which the hydraulic sensor reported heartbeat count: (1) within one beat of ground truth (the "<2" rows), (2) exactly two beats from ground truth (the "=2" rows), and (3) three or more beats from ground truth (the ">2" rows).

Figure 19:
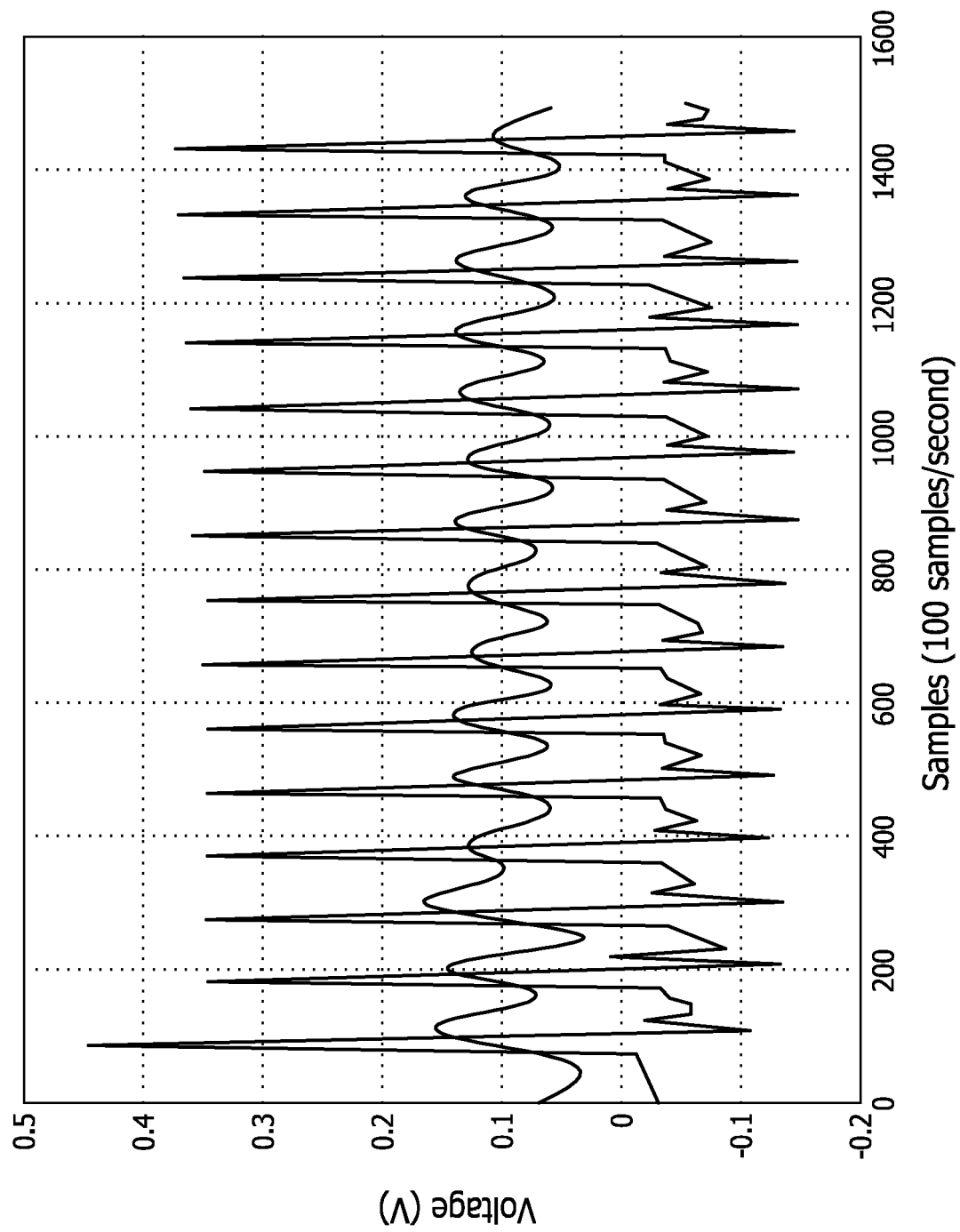
FIG. 19 shows an extracted heartbeat signal superimposed over a reference signal for a subject.
Figure 20:
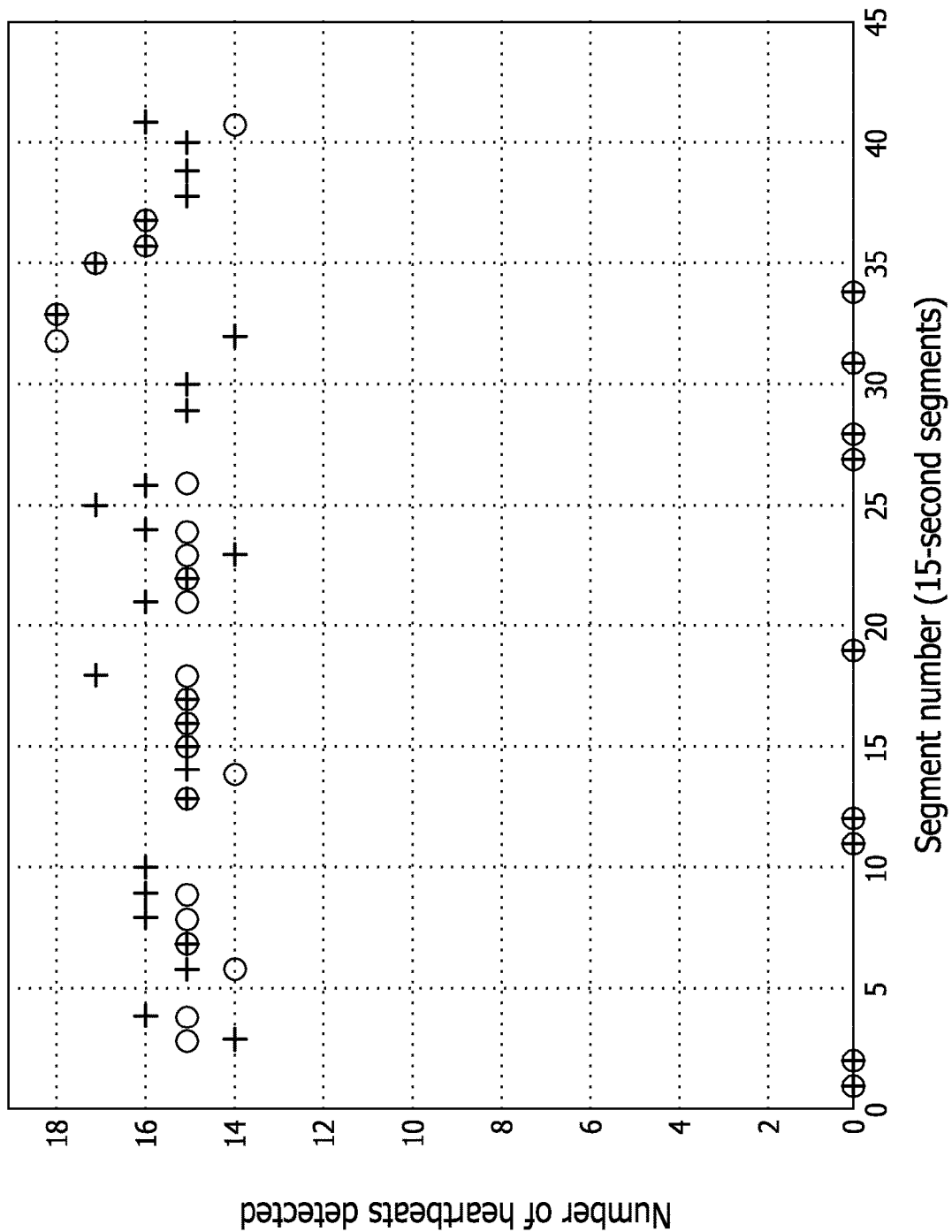
FIG. 20 shows a correspondence between extracted heartbeats relative to a reference for a subject.

FIGS. 19-20 illustrate the processing behind the entries in FIG. 21. FIG. 19 shows a particular 15-second segment (specifically, segment 39; ws=150 ms, f=1.5 Hz) of data from subject #5. FIG. 19 shows the detected heartbeats from the hydraulic sensor (the low-frequency signal), superimposed with the piezoelectric pulse sensor ground truth (with the characteristic heartbeat pattern). It is clear that the algorithm detects 15 heartbeats, which matches the ground truth exactly. The inventors note that there is some "drift" between the detected heartbeats and the ground truth, but this drift is found to tend to average-out over time. FIG. 20 shows a comparison of the number of detected heartbeats versus ground truth for the entire 10+ minute period for subject #5 (ws=150 ms, f=1.5 Hz). It is from these data that the table of FIG. 21 is generated, varying the algorithm parameters for each subject.

FIG. 20 shows the correspondence of the number of heartbeats detected via the hydraulic sensor (asterisks) and ground truth (circles). These data are for subject #5, using a WPPD window size of 150 ms and post-WPPD filter cutoff frequency of 1.5 Hz. Segments showing zero heartbeats were periods of noise due to movement.

Examining FIG. 21, the inventors note that the original parameter values in column F (ws=250 ms, f=2 Hz) work very well for subjects #1 and 4 (as do the parameters of Column I), but the results are much worse for subjects #2, 3, and 5. Column B demonstrates strong results for subjects #2-5, but is markedly worse for subject #1. The inventors conclude, then, that some set of default starting parameters may be chosen, but the ideal values depend upon the particular subject. As such, with an exemplary embodiment, algorithm parameters such as the window size for the WPPD analysis and/or the cut-off frequency for the post-WPPD low pass filtering can be adjustable, preferably on a per living being basis.

Age did not appear to adversely affect the heartbeat discrimination ability of the hydraulic sensor. In fact, the very best results were obtained from subject #5, who is closest in age to the target population (approximately 70-94). Additionally, he is the subject who reported a previous heart attack, providing further evidence that the hydraulic system will be suitable for its intended purpose.

If the ideal parameter values are known, using 15-second segments, the inventors were able to report heart rates within 8 beats per minute (bpm) of ground truth from 92.7 to 97.5% of the time. While this is not perfect, it is certainly enough to detect long-term trends in data, which is a target application. Additionally, the inventors have found that the percentage of beats detected over the entire data run for each subject indicates success rates of 95.6 to 99.8%, using the best values for ws and f identified for each subject from the table of FIG. 21.

The data thus demonstrates that the captured signal can vary from person to person, and may therefore require optimized parameters for each individual. By showing in an exemplary embodiment that one can achieve acceptable results by variation of only two parameters, the inventors note that algorithm parameters such as the window size for the WPPD analysis and/or the cut-off frequency for the post-WPPD low pass filtering can be adjustable, preferably on a per living being basis.

Further still, the inventors open the possibility of developing a method of automatically tuning the parameters based upon some initial estimate to thereby provide dynamic parameter adaptation to better fit a subject. With such an approach, one might employ manual input to define initial settings for the adaptive parameters based upon prior knowledge of the subject's medical history. Thereafter, these parameters would be dynamically adjusted. To do so, for example, the processor can gauge the regularity of the detected heart rates or inter beat distances. Because the heart rate and inter beat distances are not expected to fluctuate wildly, the inventors note that a lack of regularity can indicate a need to adjust the parameters. Thus, if a sufficient degree of irregularity is detected, the processor can adjust the parameters (e.g., incrementing or decrementing them by some specified amount), and this process can continue until sufficient regularity is found (for example, if irregularity increased after adjustment, the next adjustment can proceed in the other direction). It is expected that the rate of adaptation can take into consideration the expectation that the parameters may not need to change much for a given subject in order to achieve self-tuning. Furthermore, in another embodiment, within certain ranges of regularities (or regardless of regularity), the processor can be configured to process the sensor signal using multiple sets of parameters in parallel, and the output deemed "most regular" can be then used as it likely the one to contain the true heart rate.

Experimental Results

Clustering Analysis

A. Methodology

The transducer arrangement of FIG. 3 and the clustering technique of FIG. 22 were tested on a twin coil spring mattress with a thickness of 7 in. Four participants, whose characteristics are described in Table 5, were asked to lie down on the back for approximately 2 minutes for three consecutive times (total 6 min.). To provide ground truth, data were collected simultaneously from a pulse sensor connected to the subjects' finger. The BCG peaks were labeled manually as HB and NHB, based on the correlation between the J-peak and the pulse signal extracted from the GT signal.

TABLE 5

Participants

| Subject | Gender | Age | Weight (kg) | Height (cm) | Prior Cardiac History |
|---------|--------|-----|-------------|-------------|----------------------|
| 1 | Male | 31 | 79 | 187 | No |
| 2 | Female | 32 | 54 | 163 | Yes |
| 3 | Female | 57 | 68 | 163 | No |
| 4 | Male | 68 | 76 | 177 | Yes |

The set of features were extracted from the participants' signals as described in connection with FIG. 22. The k-means algorithm was run with k=2. The performance criteria used in the evaluation was percentage of correct detection from the confusion matrix, where correct detection refers to the number of HB (J-peaks) and NHB (the rest of the BCG peaks) effectively grouped by the clustering approach when compared to the labeled peaks. Table 6 shows the number of instances, number of features computed, and number of NHB and HB for all the participants. Finally, the beat-to-beat intervals were estimated using the J-peak locations.

TABLE 6

Instances and Features

| Subject | Number of Instances | Number of Features | Class Distribution HB | NHB |
|---------|--------------------|--------------------|----------------------|-----|
| 1 | 3768 | 3 | 964 | 2804 |
| 2 | 2138 | 3 | 466 | 1672 |
| 3 | 3464 | 3 | 621 | 2843 |
| 4 | 1359 | 3 | 307 | 1052 |

B. Results
(i) System's Ability to Capture Heartbeats

BCG signals captured by the hydraulic transducers of FIG. 3 and the clustering technique of FIG. 22 show similarities previous BCG studies. Visual inspection shows the presence of peak J and depletions I and K for all the recordings; however, peaks H, L and depletions G and M are not consistent for some segments of the BCG signals. Variation in waveforms can be explained by respiratory movements, involuntary movements and the system itself.

BCG signals for Subject 2 extracted from the four transducers are shown in FIG. 23, which illustrate the variation in waveforms due to the distance of the transducer with respect to the heart. BCG signals for Subjects 1 and 4 in FIG. 26 illustrate the variation in waveforms due to different heights and weights.

Figure 26:
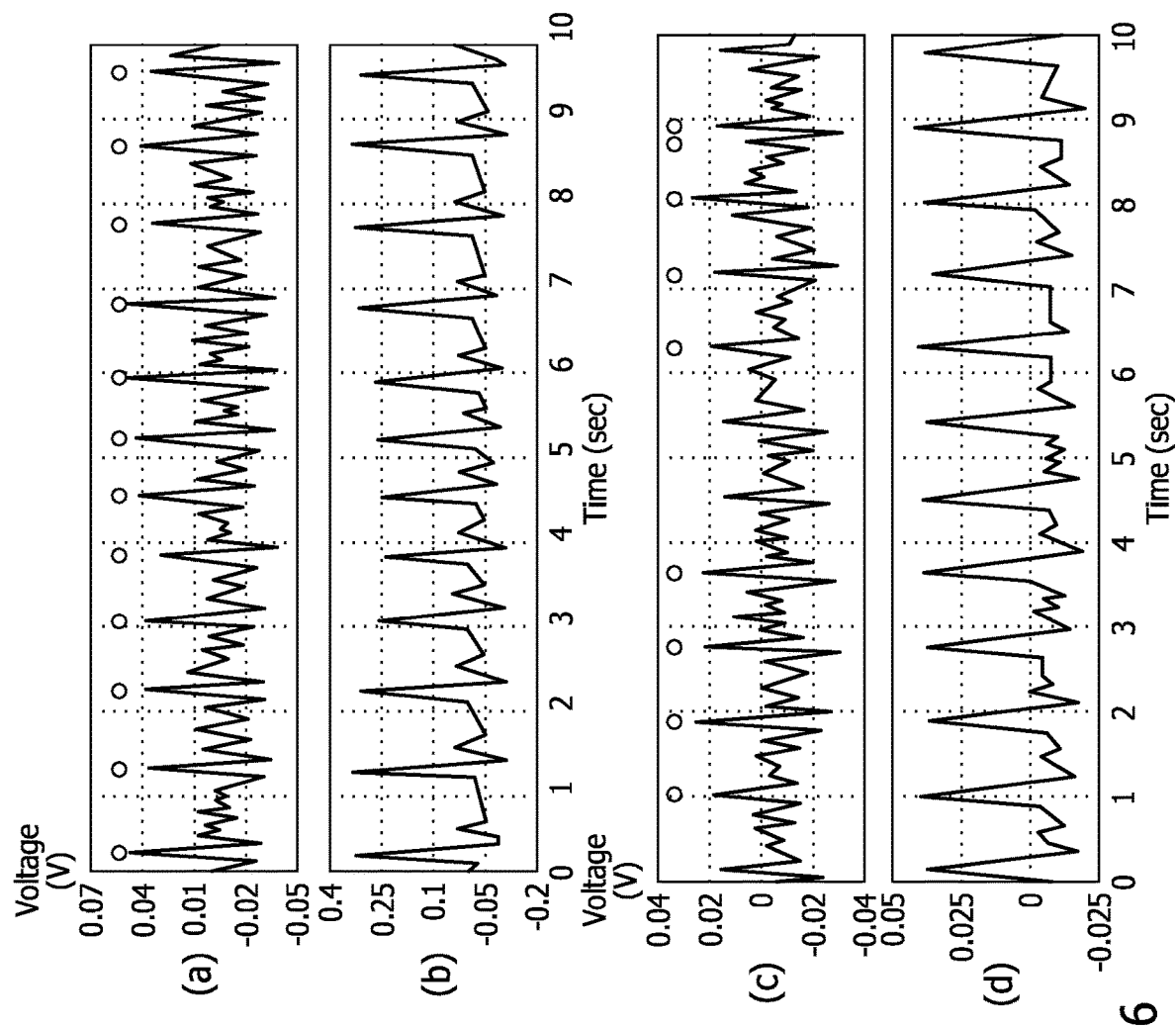
FIG. 26 shows various plots for heartbeat detection using the k-means clustering algorithm.

In FIG. 26, the J-peaks detected by the k-means clustering algorithm are marked by the circle "o". Frame (a) of FIG. 26 shows a ten-second segment of the BCG's recordings for Subject 1. Frame (c) of FIG. 26 shows a ten-second segment of the BCG's recordings for Subject 4. For reference, frames (b) and (d) of FIG. 26 show the ground truth (GT) signals extracted from a piezoresistive transducer worn on each respective subject's finger.

(ii) Heartbeat Classification from Clustering Results

FIG. 27 presents the percentage of correct classification (CC[%]) of heartbeat and non-heartbeats, as well as the number of false positives and false negatives computed from the transducer(s) which showed the occurrence of a heartbeat signal (determined by visual inspection). T1 was not included since its BCG recordings did not show the occurrence of heartbeats. The BCG of Subject 1 was captured by three transducers, while for Subjects 2 and 4, only one transducer captured their heartbeats. This is in part explained by the differences in body characteristics such as weight and can also be used for determining the position of the person on the bed.

Although percentages of correct classification for Subjects 1-3 were in the range of 97.9 to 100%, results for Subject 4 showed that some adjustment should be made. Frame (c) of FIG. 26 shows a ten-second segment of the heartbeat detection for Subject 4, where the respiratory movement is still evident and artifacts due to other causes (such as involuntary movements) are also seen in the heartbeat signal.

The number of false positives and false negatives reflects this observation. It is clear from frame (d) if FIG. 26 that the heartbeat detection algorithm does not cluster the heartbeats that are at the beginning and the end of the inhalation and exhalation, due to differences in amplitude of the J-peak. This may be because the maximal cardiac force varies from beat-to-beat as the respiratory cycle alters the filling of the heart, decreasing the amplitude of the J-peak and I-depletion, an issue that can be addressed through modifications to the clustering algorithm and/or modifications to the hydraulic transducers. For example, the transducer length and volume of fluid can be modified to suit very tall/short and heavy/light individuals. Since the system is designed for sleep monitoring, the inventors anticipate better performance when detecting the occurrence of heartbeats on sleeping segments, when the subject is still.

(iii) Beat-to-Beat Interval

Figure 28:
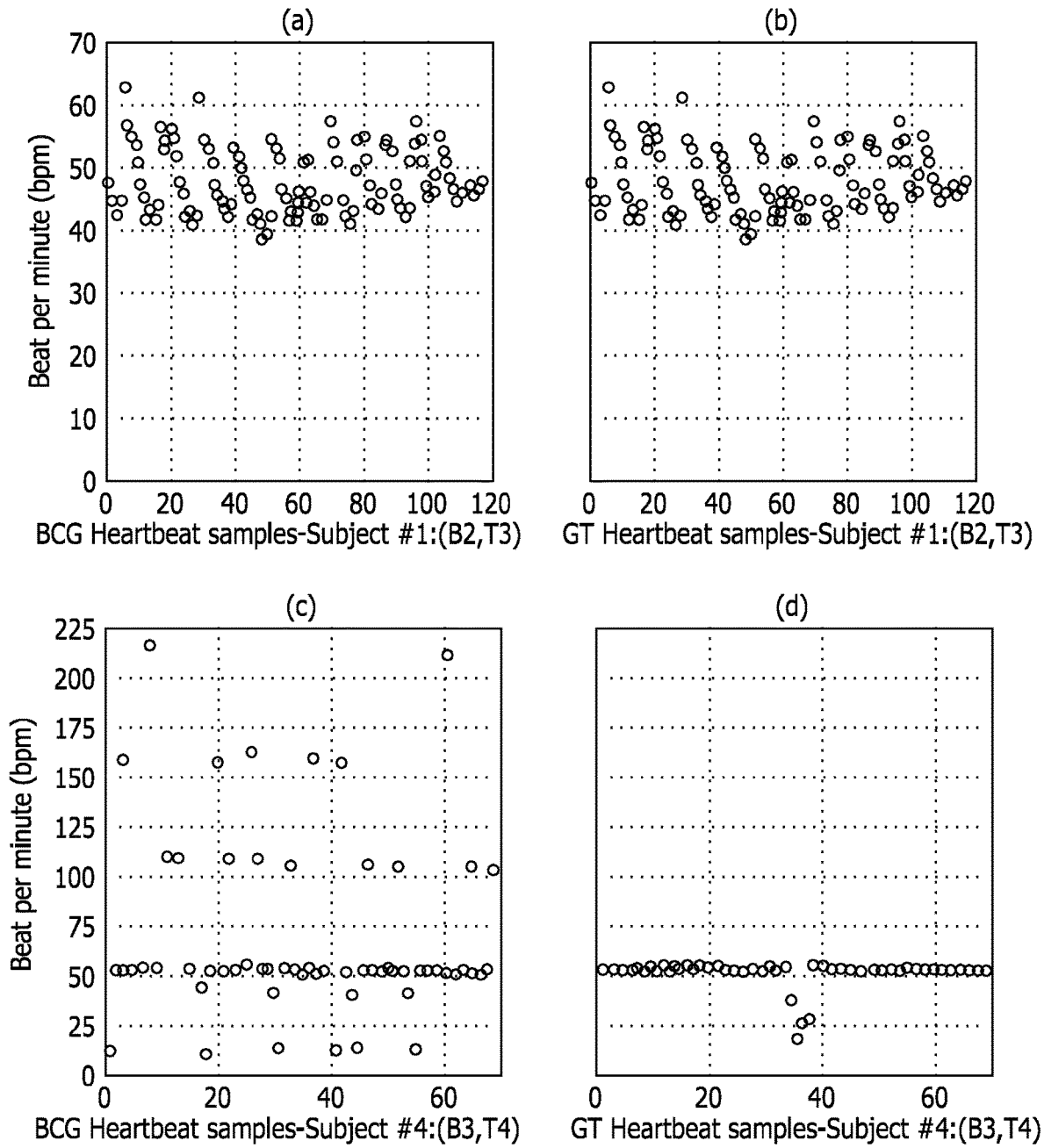
FIG. 28 shows various plots relating to beat-to-beat interval detections using the k-means clustering algorithm.

Additional information can be extracted from the J-peak locations such as beat-to-beat intervals, which open the possibility of the heart rate variability (HRV) studies. FIG. 28 shows beat-to-beat intervals for the best and worst cases of the study. Frame (a) shows the segment B2 captured by transducer T4 for Subject 1. Frame (b) shows the corresponding GT signal for Subject 1. Frame (c) shows the segment B3 captured by transducer T4 for Subject 4. Frame (d) shows the corresponding GT signal for Subject 4. Correlation between the beat-to-beat intervals extracted from the GT signal and the HBS signal can easily be observed from (a) and (b) of FIG. 28, whereas (c) and (d) of FIG. 28 shows the discrepancy. Modifications to the clustering analysis and feature extractions can improve such results.

While the invention has been described in connection with specific embodiments thereof, it will be understood that the inventive device is capable of further modifications. This patent application is intended to cover any variations, uses, or adaptations of the invention following, in general, the principles of the invention and including such departures from the present disclosure as come within known or customary practice within the art to which the invention pertains and as may be applied to the essential features herein before set forth.

What is claimed is:

1. A health monitoring system, the system comprising:
a hydraulic sensor for positioning with respect to a living being to non-invasively sense a signal, the signal comprising a heartbeat component indicative of a heartbeat pattern for the living being and a respiratory component indicative of a respiratory pattern for the living being; and
a processor for receiving the sensor signal, the processor configured to (1) generate a plurality of digital samples that are representative of the sensor signal, (2) extract a plurality of feature vectors for a plurality of prospective J-peak heartbeat candidates from the digital samples, wherein each feature vector for a prospective J-peak heartbeat candidate comprises (i) a first distance that represents a distance from a reference to a local minimum within the digital samples for that prospective J-peak heartbeat candidate, (ii) a second distance that represents a distance from a reference to a local maximum within the digital samples for that prospective J-peak heartbeat candidate, and (iii) a summation of the first and second distances for that prospective J-peak heartbeat candidate, (3) apply a clustering analysis to the extracted feature vectors to sort the prospective J-peak heartbeat candidates into a plurality of clusters, and (4) generate extracted heartbeat data based on an identification of which of the clusters contains J-peaks for the heartbeat pattern.

2. The system of claim 1 wherein the hydraulic sensor comprises a hydraulic transducer.

3. The system of claim 2 wherein the hydraulic sensor further comprises a pressure sensor, wherein the hydraulic transducer is configured to apply fluid pressure to the pressure sensor in response to the heartbeat and respiratory patterns of the living being.

4. The system of claim 3 wherein the hydraulic transducer comprises a deformable vessel filled with a fluid.

5. The system of claim 4 wherein the deformable vessel comprises a sealed portion, an open portion, and a connector, the connector configured to connect the open portion with the pressure sensor for delivering fluid from the vessel to the pressure sensor to thereby apply the fluid pressure to the pressure sensor.

6. The system of claim 5 wherein the hydraulic sensor is configured to exhibit a flat profile.

7. The system of claim 3 wherein the hydraulic sensor is positioned beneath a mattress for use by the living being in a location along the mattress that is aligned below where a torso of the living being is expected when the living being is lying on the mattress.

8. The system of claim 3 further comprising a plurality of the hydraulic sensors.

9. The system of claim 8 wherein the processor is further configured to (1) receive a plurality of sensor signals from the plurality of hydraulic sensors and (2) analyze data representative of the sensor signals to select which of the sensor signals is to be further analyzed to generate the extracted heartbeat data.

10. The system of claim 8 wherein the hydraulic sensors are positioned beneath a mattress for use by the living being in a plurality of locations along the mattress that are aligned in a range below where a torso of the living being is expected when the living being is lying on the mattress.

11. The system of claim 3 wherein the hydraulic sensor is positioned proximate to a mattress, the mattress for use by the living being.

12. The system of claim 11 wherein the hydraulic sensor is positioned beneath the mattress.

13. The system of claim 1 wherein the clustering analysis comprises a k-means clustering algorithm.

14. The system of claim 13 wherein the plurality of clusters comprises a first cluster corresponding to the J-peaks for the heartbeat pattern and a second cluster corresponding to a non-heartbeat.

15. The system of claim 13 wherein the processor comprises a signal processing circuit and a computer, the signal processing circuit configured to generate the digital samples, and wherein the computer is configured to extract the features and apply the k-means clustering algorithm.

16. The system of claim 15 wherein the signal processing circuit comprises an amplifier, a filter, and an analog to digital converter (ADC), wherein the amplifier is configured to amplify the sensor signal, wherein the filter is configured to filter the amplified sensor signal to provide anti-aliasing and noise reduction, and wherein the ADC is configured to sample the filtered amplified sensor signal to generate the digital samples.

17. The system of claim 13 wherein the processor is further configured to bandpass filter the digital samples prior to application of the k-means clustering algorithm.

18. The system of claim 1 wherein the processor is further configured to (1) determine which of the clusters contains the fewest prospective J-peak candidates, (2) select the cluster determined to contain the fewest prospective J-peak candidates as the cluster containing J-peaks for the heartbeat component, and (3) compute the heartbeat data based on the selected cluster.

19. The system of claim 18 wherein the hydraulic sensor is positioned beneath a mattress and contacts an underside of the mattress; and
wherein the hydraulic transducer exhibits a flat profile and comprises a pressure sensor and a deformable vessel filled with a fluid, wherein the deformable vessel comprises a sealed portion, an open portion, and a connector, the connector configured to connect the open portion with the pressure sensor for delivering fluid from the vessel to the pressure sensor to thereby apply fluid pressure to the pressure sensor in response to the heartbeat and respiratory patterns of the living being.

20. The system of claim 1 further comprising a sensor network for positioning in a living space of the living being, the sensor network comprising the hydraulic sensor and a plurality of other sensors, the other sensors comprising at least one motion sensor, and wherein the processor is further configured to receive and analyze signals from the other sensors to generate additional data for assessing a health status for the living being.

21. The system of claim 1 further comprising a memory; wherein the processor is further configured to time-stamp the extracted heartbeat data and store the time-stamped extracted heartbeat data in the memory to create a database of extracted heartbeat data over time for the living being; and
wherein the processor is further configured to (1) analyze data representative of a plurality of the sensor signals over time to generate extracted restlessness data for the living being, (2) time-stamp the extracted restlessness data, and (3) store the time-stamped extracted restlessness data in the memory to create a database of extracted restlessness data over time for the living being.

22. The system of claim 1 wherein the processor is further configured to (1) window the digital samples into a plurality of segments that correspond to J-peak heartbeat candidates and (2) perform the feature vector extraction with respect to each segment such that the local minima and the local maxima are localized to each segment.

23. The system of claim 1 wherein the processor is further configured to find the local minima and local maxima as inflection points in a trajectory of a waveform defined by the digital samples.

24. The system of claim 1 wherein the reference for the first and second distances is a zero voltage such that (1) the first distance represents a distance from the zero voltage to a depletion voltage and (2) the second distance represents a distance from the zero voltage to a peak voltage.

25. The system of claim 1 wherein the hydraulic sensor is positioned beneath a mattress and contacts an underside of the mattress.

26. The system of claim 25 wherein the hydraulic transducer exhibits a flat profile and comprises a pressure sensor and a deformable vessel filled with a fluid, wherein the deformable vessel comprises a sealed portion, an open portion, and a connector, the connector configured to connect the open portion with the pressure sensor for delivering fluid from the vessel to the pressure sensor to thereby apply fluid pressure to the pressure sensor in response to the heartbeat and respiratory patterns of the living being.

27. A health monitoring system, the system comprising:
a hydraulic sensor that is positioned beneath a mattress and contacts an underside of the mattress for non-invasively sensing a signal from a living being lying on the mattress, the signal comprising a heartbeat component indicative of a heartbeat pattern for the living being and a respiratory component indicative of a respiratory pattern for the living being; and
a processor for receiving the sensor signal, the processor configured to (1) perform a clustering analysis that sorts data representative of the sensor signal into a plurality of prospective J-peak candidate clusters, (2) select a cluster from among the clusters, and (3) generate extracted heartbeat data based on the selected cluster.

28. The system of claim 27 further comprising a memory, wherein the processor is further configured to store the extracted heartbeat data in the memory, the memory comprising a data structure representative of the extracted heartbeat data for the living being over time, and wherein the processor is further configured to interact with the memory to analyze the data structure to determine whether a health condition for the living being is indicated by the data structure.

29. The system of claim 28 wherein the processor is further configured to apply a filtering operation to data representative of the sensor signal to generate extracted respiratory data.

30. The system of claim 29 wherein the processor is further configured to store the extracted respiratory data in the memory, the memory further comprising a data structure representative of the extracted respiratory data for the living being over time, and wherein the processor is further configured to interact with the memory to analyze the heartbeat data structure and the respiratory data structure to determine whether any of a plurality of health conditions for the living being are indicated by the heartbeat data structure and the respiratory data structure.

31. The system of claim 30 wherein the processor is further configured to apply a condition to data representative of the sensor signal to generate extracted restlessness data for the living being, and wherein the processor is further configured to store the extracted restlessness data in the memory, the memory further comprising a data structure representative of the extracted restlessness data for the living being over time, and wherein the processor is further configured to interact with the memory to analyze the heartbeat data structure, the respiratory data structure, and the restlessness data structure to determine whether any of a plurality of health conditions for the living being are indicated by the heartbeat data structure, the respiratory data structure, and the restlessness data structure.

32. The system of claim 28 wherein the processor is further configured to apply a condition to data representative of the sensor signal to generate extracted restlessness data for the living being, and wherein the processor is further configured to store the extracted restlessness data in the memory, the memory further comprising a data structure representative of the extracted restlessness data for the living being over time, and wherein the processor is further configured to interact with the memory to analyze the heartbeat data structure and the restlessness data structure to determine whether any of a plurality of health conditions for the living being are indicated by the heartbeat data structure and the restlessness data structure.

33. The system of claim 27 wherein the hydraulic transducer exhibits a flat profile and comprises a pressure sensor and a deformable vessel filled with a fluid, wherein the deformable vessel comprises a sealed portion, an open portion, and a connector, the connector configured to connect the open portion with the pressure sensor for delivering fluid from the vessel to the pressure sensor to thereby apply fluid pressure to the pressure sensor in response to the heartbeat and respiratory patterns of the living being.

34. The system of claim 33 wherein the hydraulic sensor is positioned beneath the mattress and contacts the underside of the mattress with reference to an upper side of the mattress upon which the living being would lie.

35. The system of claim 27 wherein the processor is further configured to (1) determine which of the clusters contains the fewest prospective J-peak candidates and (2) select the cluster determined to contain the fewest prospective J-peak candidates as the cluster containing J-peaks for the heartbeat component.

36. A method comprising:
hydraulically transducing physiological movement of a living being to sense a signal, the signal comprising a heartbeat component indicative of a heartbeat pattern for the living being and a respiratory component indicative of a respiratory pattern for the living being; and
processing, by a processor, the sensed signal, the processing including the processor extracting heartbeat data from data representative of the sensor signal, wherein the processing step comprises:
the processor generating a plurality of digital samples that are representative of the sensor signal;
the processor extracting a plurality of feature vectors for a plurality of prospective J-peak heartbeat candidates from the digital samples, wherein each feature vector for a prospective J-peak heartbeat candidate comprises (i) a first distance that represents a distance from a reference to a local minimum within the digital samples for that prospective J-peak heartbeat candidate, (ii) a second distance that represents a distance from a reference to a local maximum within the digital samples for that prospective J-peak heartbeat candidate, and (iii) a summation of the first and second distances for that prospective J-peak heartbeat candidate;
the processor applying a clustering analysis to the extracted feature vectors to sort the prospective J-peak heartbeat candidates into a plurality of clusters; and
the processor generating extracted heartbeat data based on an identification of which of the clusters contains J-peaks for the heartbeat pattern.

37. The method of claim 36 further comprising:
repeating the method steps over time to sense a plurality of the signals and extract heartbeat data over time for the living being;
the processor time-stamping the extracted heartbeat data;
the processor creating a database of time-stamped heartbeat data over time for the living being;
the processor analyzing data representative of the sensed signals to generate extracted restlessness data for the living being;
the processor time-stamping the extracted restlessness data; and
the processor creating a database of time-stamped restlessness data over time for the living being.

38. The method of claim 36 wherein the processing step further comprises:
the processor windowing the digital samples into a plurality of segments that correspond to J-peak heartbeat candidates; and
the processor performing the feature vector extraction with respect to each segment such that the local minima and the local maxima are localized to each segment.

39. The method of claim 36 wherein the processing step further comprises:
the processor finding the local minima and local maxima as inflection points in a trajectory of a waveform defined by the digital samples.

40. The method of claim 36 wherein the reference for the first and second distances is a zero voltage such that (1) the first distance represents a distance from the zero voltage to a depletion voltage and (2) the second distance represents a distance from the zero voltage to a peak voltage.

41. The method of claim 36 further comprising positioning a hydraulic sensor beneath a mattress such that the hydraulic sensor contacts an underside of the mattress, wherein the hydraulic transducing step is performed by the positioned hydraulic sensor.

42. The method of claim 36 wherein the applying step comprises:
the processor determining which of the clusters contains the fewest prospective J-peak candidates; and
the processor selecting the cluster determined to contain the fewest prospective J-peak candidates as the cluster containing J-peaks for the heartbeat component; and wherein the generating step comprises the processor computing the heartbeat data based on the selected cluster.

* * * * *